(12) United States Patent
Budzik et al.

(10) Patent No.: US 7,932,247 B2
(45) Date of Patent: Apr. 26, 2011

(54) M₃ MUSCARINIC ACETYLCHOLINE RECEPTOR ANTAGONISTS

(75) Inventors: Brian W. Budzik, Collegeville, PA (US); Anthony W. J. Cooper, Stevenage (GB); Jian Jin, Collegeville, PA (US); Dramane I. Laine, King of Prussia, PA (US); Brent W. McCleland, King of Prussia, PA (US); Michael R. Palovich, King of Prussia, PA (US); Ralph A. Rivero, Collegeville, PA (US); Yonghui Wang, Collegeville, PA (US); Haibo Xie, King of Prussia, PA (US); Chongjie Zhu, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 747 days.

(21) Appl. No.: 11/719,336

(22) PCT Filed: Nov. 15, 2005

(86) PCT No.: PCT/US2005/041346
§ 371 (c)(1),
(2), (4) Date: May 15, 2007

(87) PCT Pub. No.: WO2006/055553
PCT Pub. Date: May 26, 2006

(65) Prior Publication Data
US 2009/0149447 A1    Jun. 11, 2009

Related U.S. Application Data

(60) Provisional application No. 60/627,986, filed on Nov. 15, 2004.

(51) Int. Cl.
A61K 31/496 (2006.01)
A61K 31/551 (2006.01)
A61K 31/5377 (2006.01)
C07D 401/12 (2006.01)
C07D 403/12 (2006.01)
C07D 409/14 (2006.01)
C07D 413/14 (2006.01)
C07D 487/10 (2006.01)

(52) U.S. Cl. .............. 514/218; 514/235.8; 514/252.11; 514/253.01; 514/254.08; 540/575; 544/121; 544/230; 544/357; 544/360; 544/364; 544/373; 544/400

(58) Field of Classification Search ............... None
See application file for complete search history.

(56) References Cited

U.S. PATENT DOCUMENTS

| | | | |
|---|---|---|---|
| 5,510,478 A | 4/1996 | Sabb | |
| 7,232,841 B2 | 6/2007 | Busch-Petersen et al. | |
| 7,276,521 B2 | 10/2007 | Busch-Petersen et al. | |
| 7,439,255 B2 | 10/2008 | Wan et al. | |
| 7,488,827 B2 | 2/2009 | Laine et al. | |
| 7,495,010 B2 | 2/2009 | Belmonte et al. | |
| 7,498,440 B2 | 3/2009 | Laine et al. | |
| 7,507,753 B2 | 3/2009 | Cho et al. | |
| 7,563,803 B2 | 7/2009 | Wan et al. | |
| 7,576,096 B2 | 8/2009 | Busch-Petersen et al. | |
| 7,579,345 B2 | 8/2009 | Busch-Petersen et al. | |
| 7,579,361 B2 | 8/2009 | Busch-Petersen et al. | |
| 7,598,267 B2 | 10/2009 | Laine et al. | |
| 2005/0277676 A1 | 12/2005 | Laine et al. | |
| 2006/0160844 A1 | 7/2006 | Belmonte et al. | |
| 2006/0178395 A1 | 8/2006 | Belmonte et al. | |
| 2007/0135478 A1 | 6/2007 | Palovich et al. | |
| 2007/0149598 A1 | 6/2007 | Busch-Petersen et al. | |
| 2007/0179180 A1 | 8/2007 | Busch-Petersen et al. | |
| 2007/0179184 A1 | 8/2007 | Busch-Petersen et al. | |
| 2007/0185088 A1 | 8/2007 | Busch-Petersen et al. | |
| 2007/0185090 A1 | 8/2007 | Busch-Petersen et al. | |
| 2007/0185148 A1 | 8/2007 | Busch-Petersen et al. | |
| 2007/0293531 A1 | 12/2007 | Busch-Petersen et al. | |
| 2008/0249127 A1 | 10/2008 | Laine et al. | |
| 2008/0287487 A1 | 11/2008 | Cooper et al. | |
| 2009/0076061 A1 | 3/2009 | Busch-Petersen et al. | |
| 2009/0124653 A1 | 5/2009 | Laine et al. | |
| 2009/0142279 A1 | 6/2009 | Budzik et al. | |
| 2009/0149447 A1 | 6/2009 | Budzik et al. | |
| 2009/0253908 A1 | 10/2009 | Budzik et al. | |
| 2009/0258858 A1 | 10/2009 | Busch-Petersen et al. | |
| 2009/0275604 A1 | 11/2009 | Wan et al. | |

FOREIGN PATENT DOCUMENTS

| | | |
|---|---|---|
| EP | 1 295 867 A | 3/2003 |
| EP | 1 331 010 A | 7/2003 |
| WO | 02/44137 A | 6/2002 |
| WO | 03/033483 * | 4/2003 |
| WO | WO2005/087236 A1 | 9/2005 |
| WO | 2006/062883 | 6/2006 |
| WO | 2006/062931 | 6/2006 |
| WO | 2006/065755 | 6/2006 |
| WO | 2006/065788 | 6/2006 |
| WO | 2007/018508 | 2/2007 |
| WO | 2007/018514 | 2/2007 |

OTHER PUBLICATIONS

Pauwels et al., Am J Respir Crit Care Med, vol. 163, p. 1256-1276 (2001).
Caufield, Pharmac. Ther., vol. 58, p. 319-379 (1993).
Fryer and Jacoby, Am J. Respir Crit Care Med., p. 154-160 (1998).
Seifart et al., Expert Opinion, Emerging Drugs, (14) 1, pp. 181-194 (2009).
Gross, N, European Journal of Pharmacology, 533 (2006), pp. 36-39.
Cazzola et al., European Respiratory Journal, (34), p. 1-13 (2009).
Most Recent Office Action U.S. Appl. No. 10/598,743, Oct. 6, 2010.

* cited by examiner

*Primary Examiner* — Emily Bernhardt
(74) *Attorney, Agent, or Firm* — Dara L. Dinner; Theodore Furman

(57) ABSTRACT

Muscarinic Acetylcholine receptor antagonists and methods of using them are provided.

4 Claims, No Drawings

M₃ MUSCARINIC ACETYLCHOLINE RECEPTOR ANTAGONISTS

This application is a 371 of International Application No. PCT/US2005/041346, filed 15 Nov. 2005, which claims priority of U.S. Provisional Application No. 60/627,986, filed 15 Nov. 2004.

FIELD OF THE INVENTION

This invention relates to novel derivatives of biaryl amines, pharmaceutical compositions, processes for their preparation, and use thereof in treating $M_3$ muscarinic acetylcholine receptor mediated diseases.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed M1-M5, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, M3 mAChRs mediate contractile responses. For review, please see Caulfield (1993 Pharmac. Ther. 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 Am J Respir Crit Care Med 158 (5, pt 3) S 154-60).

Three subtypes of mAChRs have been identified as important in the lungs, M1, M2 and M3 mAChRs. The M3 mAChRs, located on airway smooth muscle, mediate muscle contraction. Stimulation of M3 mAChRs activates the enzyme phospholipase C via binding of the stimulatory G protein Gq/11 (Gs), leading to liberation of phosphatidyl inositol-4,5-bisphosphate, resulting in phosphorylation of contractile proteins. M3 mAChRs are also found on pulmonary submucosal glands. Stimulation of this population of M3 mAChRs results in mucus secretion.

M2 mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal M2 mAChRs are located on postganglionic parasympathetic nerves. Under normal physiologic conditions, neuronal M2 mAChRs provide tight control of acetylcholine release from parasympathetic nerves. Inhibitory M2 mAChRs have also been demonstrated on sympathetic nerves in the lungs of some species. These receptors inhibit release of noradrenaline, thus decreasing sympathetic input to the lungs.

M1 mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory M2 muscarinic acetylcholine autoreceptor function on parasympathetic nerves supplying the pulmonary smooth muscle, causing increased acetylcholine release following vagal nerve stimulation (Fryer et al. 1999 Life Sci 64 (6-7) 449-55). This mAChR dysfunction results in airway hyperreactivity and hyperresponsiveness mediated by increased stimulation of M3 mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 Am. J. Respir. Crit. Care Med. 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anti-cholinergic use.

SUMMARY OF THE INVENTION

This invention provides for a method of treating a muscarinic acetylcholine receptor (mAChR) mediated disease, wherein acetylcholine binds to an $M_3$ mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

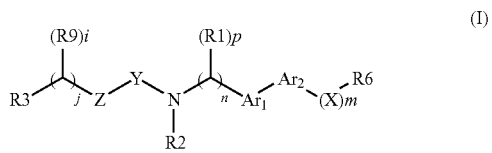

(I)

wherein

Ar1 and Ar2, are independently, selected from the group consisting of optionally substituted phenyl and optionally substituted monocyclic heteroaryl;

R6 is $NR_7R_8$, or an optionally substituted saturated or partially unsaturated 4-10 membered ring system in which one or more rings contain one or more secondary nitrogens, tertiary nitrogens, or quaternary ammonium nitrogens, and optionally contain one or more O, or S;

X is C(R1)p, or C(O); wherein, when X is C(R1)p, m is an integer from 0 to 3; when X is C(O), m is 1;

p is an integer from 0 to 2;
i is an integer from 0 to 2;
n is an integer from 0 to 3;
j is an integer from 0 to 3;
Y is C(O), S(O)q, HNC(O), OC(O), or $CH_2$; wherein, q is 1 or 2;

R1, R2, and R9 are independently selected from the group consisting of hydrogen, optionally substituted $C_1$-$C_{10}$ alkyl, optionally substituted $C_3$-$C_{10}$ cycloalkyl, optionally substituted $C_3$-$C_{10}$ cycloalkyl alkyl, optionally substituted heterocylic, optionally substituted heterocyclicalkyl, optionally substituted alkenyl, optionally substituted aryl, optionally substituted aryl alkyl, optionally substituted heteroaryl, and optionally substituted heteroaryl alkyl;

Z is selected from the group consisting of optionally substituted aryl, optionally substituted heteroaryl, optionally substituted alkenyl, optionally substituted $C_1$-$C_{10}$ alkyl, optionally substituted $C_3$-$C_{10}$ cycloalkyl, optionally substituted $C_3$-$C_{10}$ cycloalkyl alkyl, optionally substituted aryl alkyl, and optionally substituted heteroaryl alkyl;

R3 is $NR_4R_5$, or an optionally substituted saturated or unsaturated 4-10 membered ring system in which one or more rings contain one or more secondary or tertiary nitrogens, and optionally contain one or more O, or S;

$R_4$ and $R_5$, are independently, selected from the group consisting of hydrogen, optionally substituted $C_{1-10}$ alkyl, optionally substituted alkenyl, optionally substituted $C_3$-$C_{10}$ cycloalkyl, optionally substituted $C_3$-$C_{10}$ cycloalkyl alkyl, optionally substituted aryl, optionally substituted arylalkyl, optionally substituted heteroaryl, optionally substituted heteroarylalkyl, optionally substituted heterocyclic, and optionally substituted heterocyclicalkyl; or $R_4$ and $R_5$ together with the nitrogen to which they are attached form a 5 to 7 membered ring which may optionally comprise an additional heteroatom selected from O, N and S;

$R_7$ and $R_8$, are independently, selected from the group consisting of hydrogen, optionally substituted $C_{1-10}$ alkyl, optionally substituted alkenyl, optionally substituted $C_3$-$C_{10}$ cycloalkyl, optionally substituted $C_3$-$C_{10}$ cycloalkyl alkyl, optionally substituted aryl, optionally substituted arylalkyl, optionally substituted heteroaryl, optionally substituted heteroarylalkyl, optionally substituted heterocyclic, and optionally substituted heterocyclicalkyl; or $R_7$ and $R_8$ together with the nitrogen to which they are attached form a 5 to 7 member ring which may optionally comprise an additional heteroatom selected from O, N and S;

or a pharmaceutically acceptable salt thereof.

DETAILED DESCRIPTION

The present invention includes all hydrates, solvates, complexes and prodrugs of the compounds of this invention. Prodrugs are any covalently bonded compounds that release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in Eur. J. Biochem., 158, 9 (1984).

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

As used herein, "optionally substituted" unless specifically defined shall mean such groups as hydrogen; halogen, such as fluorine, chlorine, bromine or iodine; cyano; hydroxy; hydroxy substituted $C_{1-10}$ alkyl; cyano substituted $C_{1-10}$ alkyl; $C_{1-10}$ alkoxy, such as methoxy or ethoxy; $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_7R_8$ group; $NHC(O)R_7$; $C(O)NR_7R_8$; $C(O)R7$; $C(O)OH$; $S(O)_2NR_7R_8$; $NHS(O)_2R_7$, $C_{1-10}$ alkyl, such as methyl, ethyl, propyl, isopropyl, or t-butyl; alkenyl, such as ethenyl, 1-propenyl, 2-propenyl, or 2-methyl-1-propenyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocyclic alkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted alkyl amino, such as in the $NR_7R_8$ group; $C_{1-10}$ alkyl, or halosubstituted $C_{1-10}$ alkyl, such as $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid and mandelic acid.

The following terms, as used herein, refer to:

"halo" or "halogen"—chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, isopropyl, n-butyl, sec-butyl, iso-butyl, tert-butyl, n-pentyl and the like.

"$C_1$-$C_{10}$ alkoxy" includes straight and branched chain radicals of the likes of —O—$CH_3$, —O—$CH_2CH_3$, and the n-propoxy, isopropoxy, n-butoxy, sec-butoxy, isobutoxy, tert-butoxy, pentoxy, and hexoxy, and the like.

"$C_3$-$C_{10}$ cycloalkyl" is used herein to mean cyclic moiety, including but not limited to cyclopropyl, cyclopentyl, cyclohexyl, and the like.

"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"secondary nitrogen" is used herein to mean a nitrogen directly connected to one hydrogen, one optionally substituted carbon, and one optionally substituted carbon, C(O), or S(O)m'; where in m' is 1 or 2.

"tertiary nitrogen" is used herein to mean a nitrogen directly connected to two independent optionally substituted carbons, and one optionally substituted carbon, C(O), or S(O)m'; where in m' is 1 or 2.

"quaternary ammonium nitrogen" is used herein to mean a nitrogen directly connected to four independent optionally substituted carbons.

"arylalkyl" or "heteroarylalkyl" or "heterocyclicalkyl" is used herein to mean $C_1$-$C_{10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl" refers to the fully oxidized $S(O)_2$ moiety.

The preferred compounds of Formula I include those compounds wherein:

Ar1 and Ar2, are independently, selected from the group consisting of optionally substituted phenyl and optionally substituted monocyclic heteroaryl;

R6 is an optionally substituted saturated or partially unsaturated 4-10 membered ring system in which one or more rings contain one or more secondary or tertiary nitrogens;

X is C(R1)p;
p is 2;
m is an integer from 0 to 3;
i is 2;
n is an integer from 1 to 3;
j is an integer from 0 to 3;
Y is C(O), or S(O)q; wherein, q is 1 or 2;
R1 is hydrogen
R9 is hydrogen
R2 is selected from the group consisting of hydrogen, optionally substituted $C_1$-$C_{10}$ alkyl, optionally substituted alkenyl, optionally substituted $C_3$-$C_{10}$ cycloalkyl, optionally substituted $C_3$-$C_{10}$ cycloalkyl alkyl, optionally substituted heterocyclic, optionally substituted heterocyclicalkyl, optionally substituted aryl, optionally substituted aryl alkyl, optionally substituted heteroaryl, and optionally substituted heteroaryl alkyl;

Z is selected from the group consisting of optionally substituted aryl, optionally substituted heteroaryl, optionally substituted aryl alkyl, and optionally substituted heteroaryl alkyl;

R3 is $NR_4R_5$, or an optionally substituted saturated or unsaturated 4-10 membered ring system in which one or more rings contain one or more secondary or tertiary nitrogens, and optionally contain one or more O, or S;

$R_4$ and $R_5$, are independently, selected from the group consisting of hydrogen, optionally substituted $C_{1-10}$ alkyl, optionally substituted alkenyl, optionally substituted $C_3$-$C_{10}$ cycloalkyl, optionally substituted $C_3$-$C_{10}$ cycloalkyl alkyl, optionally substituted aryl, optionally substituted arylalkyl, optionally substituted heteroaryl, optionally substituted heteroarylalkyl, optionally substituted heterocyclic, and optionally substituted heterocyclicalkyl; or $R_4$ and $R_5$ together with the nitrogen to which they are attached form a 5 to 7 membered ring which may optionally comprise an additional heteroatom selected from O, N and S;

or a pharmaceutically acceptable salt thereof.

More preferred are those compounds where:

Ar1 and Ar2, are independently, selected from the group consisting of optionally substituted phenyl and optionally substituted monocyclic heteroaryl;

R6 is an optionally substituted saturated or partially unsaturated 5-8 membered ring system in which one or more rings contain one or more secondary or tertiary nitrogens;

X is C(R1)p;
p is 2;
m is 1;
i is 2;
n is 1;
j is 1, or 0;
Y is C(O), or S(O)q; wherein, q is 1 or 2;
R1 is hydrogen
R9 is hydrogen
R2 is selected from the group consisting of hydrogen, optionally substituted $C_1$-$C_{10}$ alkyl, optionally substituted alkenyl, optionally substituted $C_3$-$C_{10}$ cycloalkyl, optionally substituted $C_3$-$C_{10}$ cycloalkyl alkyl, optionally substituted heterocylic, optionally substituted heterocyclicalkyl, optionally substituted aryl alkyl, and optionally substituted heteroaryl alkyl;

Z is selected from the group consisting of optionally substituted aryl, optionally substituted heteroaryl, optionally substituted aryl alkyl, and optionally substituted heteroaryl alkyl;

R3 is $NR_4R_5$, or an optionally substituted saturated or unsaturated 4-10 membered ring system in which one or more rings contain one or more secondary or tertiary nitrogens, and optionally contain one or more O, or S;

$R_4$ and $R_5$, are independently, selected from the group consisting of hydrogen, optionally substituted $C_{1-10}$ alkyl, optionally substituted alkenyl, optionally substituted $C_3$-$C_{10}$ cycloalkyl, optionally substituted $C_3$-$C_{10}$ cycloalkyl alkyl, optionally substituted aryl, optionally substituted arylalkyl, optionally substituted heteroaryl, optionally substituted heteroarylalkyl, optionally substituted heterocyclic, and optionally substituted heterocyclicalkyl; or $R_4$ and $R_5$ together with the nitrogen to which they are attached form a 5 to 7 membered ring which may optionally comprise an additional heteroatom selected from O, N and S;

or a pharmaceutically acceptable salt thereof.

The preferred compounds are selected from the group consisting of:

N-[(6-fluoro-3'-{[(3S)-3-methyl-1-piperazinyl]methyl}-3-biphenylyl)methyl]-3-[(4-methyl-1-piperazinyl)methyl]benzamide tetra-trifluoroacetate;

3-[(4-methyl-1-piperazinyl)methyl]-N-{[3'-(1-piperazinylmethyl)-3-biphenylyl]methyl}benzamide tetra-trifluoroacetate;

N-({3'-[(1S,4S)-2,5-diazabicyclo[2.2.1]hept-2-ylmethyl]-3-biphenylyl}methyl)-3-[(4-methyl-1-piperazinyl)methyl]benzamide tetra-trifluoroacetate;

3-[(4-methyl-1-piperazinyl)methyl]-N-({3'-[(3-methyl-1-piperazinyl)methyl]-3-biphenylyl)methyl)benzamide tetra-trifluoroacetate;

N-[(6-(methyloxy)-3'-{[(3S)-3-methyl-1-piperazinyl]methyl}-3-biphenylyl)methyl]-3-[(4-methyl-1-piperazinyl)methyl]benzamide tetra-trifluoroacetate;

N-[(6-fluoro-3'-{[(3S)-3-methyl-1-piperazinyl]methyl}-3-biphenylyl)methyl]-3-(1-piperazinylmethyl)benzamide tetra-trifluoroacetate;

N-[(6-fluoro-3'-{[(3S)-3-methyl-1-piperazinyl]methyl}-3-biphenylyl)methyl]-3-(hexahydro-1H-1,4-diazepin-1-ylmethyl)benzamide tetra-trifluoroacetate;

3-[(1S,4S)-2,5-diazabicyclo[2.2.1]hept-2-ylmethyl]-N-[(6-fluoro-3'-{[(3S)-3-methyl-1-piperazinyl]methyl})-3-biphenylyl)methyl]benzamide tetra-trifluoroacetate;

N-[(6-fluoro-3'-{[(3S)-3-methyl-1-piperazinyl]methyl}-3-biphenylyl)methyl]-3-[(3-methyl-1-piperazinyl)methyl]benzamide tetra-trifluoroacetate;

3-{[4-(3-cyanopropyl)-1-piperazinyl]methyl}-N-[(6-fluoro-3'-{[(3S)-3-methyl-1-piperazinyl]methyl}-3-biphenylyl)methyl]benzamide tetra-trifluoroacetate;

4-([3-({[(6-fluoro-3'-{[(3S)-3-methyl-1-piperazinyl]methyl}-3-biphenylyl)methyl]amino}carbonyl)phenyl]methyl}-2-piperazinecarboxamide tetra-trifluoroacetate;

N-[(6-fluoro-3'-[[(3S)-3-methyl-1-piperazinyl]methyl}-3-biphenylyl)methyl]-3-({4-[3-(methyloxy)propyl]-1-piperazinyl}methyl)benzamide tetra trifluoroacetate;

N-[(6-fluoro-3'-{[(3S)-3-methyl-1-piperazinyl]methyl}-3-biphenylyl)methyl]-3-[(4-methyl-1-piperidinyl)methyl]benzamide tri-trifluoroacetate;

N-[(6-fluoro-3'-{[(3S)-3-methyl-1-piperazinyl]methyl}-3-biphenylyl)methyl]-3-({4-[2-(phenyloxy)ethyl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-{[4-(3-hydroxypropyl)-1-piperazinyl]methyl}benzamide tetra-trifluoroacetate;

3-({2-[(dimethylamino)methyl]-1-piperidinyl}methyl)-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl})-3-biphenylyl)methyl]-3-(4-morpholinylmethyl)benzamide tri-trifluoroacetate;

3-[(2,5-dimethyl-1-piperazinyl)methyl]-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-{[(1S,4S)-5-methyl-2,5-diazabicyclo[2.2.1]hept-2-yl]methyl}benzamide tetra-trifluoroacetate;

N-[(6-fluoro-3'-{[(3S)-3-methyl-1-piperazinyl]methyl}-3-biphenylyl)methyl]-3-[(4-formyl-1-piperazinyl)methyl]benzamide tri-trifluoroacetate;

3-{[[3-(dimethylamino)propyl](methyl)amino]methyl}-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-{[4-(1-methyl-4-piperidinyl)-1-piperazinyl]methyl)benzamide penta-trifluoroacetate;

3-{[[2-(dimethylamino)ethyl](methyl)amino]methyl}-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[(2E)-3-phenyl-2-propen-1-yl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-[(4-methylhexahydro-1H-1,4-diazepin-1-yl)methyl]benzamide tetra-trifluoroacetate;

3-[(dimethylamino)methyl]-N-[(6-fluoro-3'-{[(3S)-3-methyl-1-piperazinyl]methyl}-3-biphenylyl)methyl]benzamide tri-trifluoroacetate;

N-[(6-fluoro-3'-{[(3S)-3-methyl-1-piperazinyl]methyl}-3-biphenylyl)methyl]-3-({4-[2-(4-morpholinyl)ethyl]-1-piperazinyl)methyl)benzamide penta-trifluoroacetate;

3-[(diethylamino)methyl]-N-[(6-fluoro-3'-{[(3S)-3-methyl-1-piperazinyl]methyl}-3-biphenylyl)methyl]benzamide tri-trifluoroacetate;

3-({4-[2-(dimethylamino)ethyl]-1-piperidinyl}methyl)-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[2-(1-pyrrolidinyl)ethyl]-1-piperazinyl)methyl)benzamide penta-trifluoroacetate;

N-[(6-fluoro-3'-{[(3S)-3-methyl-1-piperazinyl]methyl})-3-biphenylyl)methyl]-3-{[methyl(1-methyl-3-pyrrolidinyl)amino]methyl}benzamide tetra-trifluoroacetate;

N-[(6-fluoro-3'-{[(3S)-3-methyl-1-piperazinyl]methyl}-3-biphenylyl)methyl]-3-(1-piperidinylmethyl)benzamide tri-trifluoroacetate;

N-[(6-fluoro-3'-{[(3S)-3-methyl-1-piperazinyl]methyl}-3-biphenylyl)methyl]-3-[(1-methyl-1,7-diazaspiro[4.4]non-7-yl)methyl]benzamide tetra-trifluoroacetate;

3-{[bis(phenylmethyl)amino]methyl}-N-[(6-fluoro-3'-{[(3S)-3-methyl-1-piperazinyl]methyl}-3-biphenylyl)methyl]benzamide tri-trifluoroacetate;

3-(dimethylamino)-N-({3'-[(3-methyl-1-piperazinyl)methyl]-3-biphenylyl}methyl)benzamide tri-trifluoroacetate;

3-(dimethylamino)-N-{[3'-(1-piperazinylmethyl)-3-biphenylyl]methyl}benzamide tri-trifluoroacetate;

N-({3'-[(1S,4S)-2,5-diazabicyclo[2.2.1]hept-2-ylmethyl]-3-biphenylyl}methyl)-3-(dimethylamino)benzamide tri-trifluoroacetate;

3-amino-N-{[3'-(1-piperazinylmethyl)-3-biphenylyl]methyl}benzamide tri-trifluoroacetate;

3-amino-N-({3'-[(1S,4S)-2,5-diazabicyclo[2.2.1]hept-2-ylmethyl]-3-biphenylyl}methyl)benzamide tri-trifluoroacetate;

N-1-[(6-fluoro-3'-{[(3S)-3-methyl-1-piperazinyl]methyl}-3-biphenylyl)methyl]-3-(4-piperidinylmethyl)benzamide;

N-[(3'-{[(3S)-3-methyl-1-piperazinyl]methyl}-3-biphenylyl)methyl]-3-(4-piperidinylmethyl)benzamide;

N-{[3'-(1-piperazinylmethyl)-3-biphenylyl]methyl}-3-(3-pyridinyl)benzamide;

N-[(6-fluoro-3'-{[(3S)-3-methyl-1-piperazinyl]methyl}-3-biphenylyl)methyl]-3-[(1-methyl-4-piperidinyl)methyl]benzamide trifluoroacetate;

N-{[6-fluoro-3'-(1-piperazinylmethyl)-3-biphenylyl]methyl}-3-(4-piperidinylmethyl)benzamide;

N-[(4-fluoro-3'-{[(3S)-3-methyl-1-piperazinyl]methyl}-3-biphenylyl)methyl]-3-(4-piperidinylmethyl)benzamide;

N-[(6-fluoro-3'-{[(3S)-3-methyl-1-piperazinyl]methyl}-3-biphenylyl)methyl]-4-(4-piperidinylmethyl)benzamide trifluoroacetate;

N-{[3-(6-{[(3S)-3-methyl-1-piperazinyl]methyl}-2-pyridinyl)phenyl]methyl}-3-(4-piperidinylmethyl)benzamide trifluoroacetate;

N-[(6-fluoro-3'-{[(3S)-3-methyl-1-piperazinyl]methyl}-3-biphenylyl)methyl]-N-(2-{[2-(methyloxy)ethyl]oxy}ethyl)-3-(4-piperidinylmethyl)benzamide;

N-[(6-fluoro-3'-{[(3S)-3-methyl-1-piperazinyl]methyl}-3-biphenylyl)methyl]-N-[3-(phenyloxy)propyl]-3-(4-piperidinylmethyl)benzamide;

N-[(6-fluoro-3'-{[(3S)-3-methyl-1-piperazinyl]methyl}-3-biphenylyl)methyl]-3-(4-piperidinyl)benzamide;

N-[(6-fluoro-3'-{[(3S)-3-methyl-1-piperazinyl]methyl}-3-biphenylyl)methyl]-N-[2-(methyloxy)ethyl]-3-(4-piperidinylmethyl)benzamide;

N-{[5-(3-{[(3S)-3-methyl-1-piperazinyl]methyl}phenyl)-2-thienyl]methyl}-4-(4-piperidinylmethyl)benzamide;

N-[(6-fluoro-3'-{[(3S)-3-methyl-1-piperazinyl]methyl}-3-biphenylyl)methyl]-N-nonyl-3-(4-piperidinylmethyl)benzamide;

N-[(6-fluoro-3'-{[(3S)-3-methyl-1-piperazinyl]methyl}-3-biphenylyl)methyl]-N-[3-(methyloxy)propyl]-3-(4-piperidinylmethyl)benzamide;

N-[(6-fluoro-3'-{[(3S)-3-methyl-1-piperazinyl]methyl}-3-biphenylyl)methyl]-N-(3-phenylpropyl)-3-(4-piperidinylmethyl)benzamide;

N-[(4-fluoro-3'-{[(3S)-3-methyl-1-piperazinyl]methyl}-3-biphenylyl)methyl]-3-(4-piperidinyl)benzamide;

N-[(6-fluoro-3'-{[(3S)-3-methyl-1-piperazinyl]methyl}-3-biphenylyl)methyl]-N-hexyl-3-(4-piperidinylmethyl)benzamide; phenylmethyl (2S)-4-({2'-fluoro-5'-[({[3-(4-piperidinylmethyl)phenyl]carbonyl}amino)methyl]-3-biphenylyl}methyl)-2-methyl-1-piperazinecarboxylate trifluoroacetate;

N-[(6-fluoro-3'-{[(3S)-3-methyl-1-piperazinyl]methyl}-3-biphenylyl)methyl]-N-(phenylmethyl)-3-(4-piperidinylmethyl)benzamide;

N-{[3-(5-{[(3S)-3-methyl-1-piperazinyl]methyl}-2-thienyl)phenyl]methyl}-3-(4-piperidinylmethyl)benzamide trifluoroacetate;

N-[(6-fluoro-3'-{[(3S)-3-methyl-1-piperazinyl]methyl}-3-biphenylyl)methyl]-N-methyl-3-(4-piperidinylmethyl)benzamide;

N-[(3'-{[(3S)-3,4-dimethyl-1-piperazinyl]methyl}-6-fluoro-3-biphenylyl)methyl]-3-(4-piperidinylmethyl)benzamide;

(2S)-4-({2'-fluoro-5'-[({[3-(4-piperidinylmethyl)phenyl]carbonyl-amino)methyl]-3-biphenylyl}methyl)-1,1,2-trimethylpiperazin-1-ium bromide;

N-{[3'-(aminomethyl)-6-fluoro-3-biphenylyl]methyl}-3-(4-piperidinylmethyl)benzamide trifluoroacetate;

N-ethyl-N-[(6-fluoro-3'-{[(3S)-3-methyl-1-piperazinyl]methyl)-3-biphenylyl)methyl]-3-(4-piperidinylmethyl)benzamide;

N-(cyclohexylmethyl)-N-[(6-fluoro-3'-{[(3S)-3-methyl-1-piperazinyl]methyl}3-biphenylyl)methyl]-3-(4-piperidinylmethyl)benzamide;

N-(cyclopropylmethyl)-N-[(6-fluoro-3'-{[(3S)-3-methyl-1-piperazinyl]methyl}-3-biphenylyl)methyl]-3-(4-piperidinylmethyl)benzamide; and N-[(3'-{[(3S)-3,4-dimethyl-1-piperazinyl]methyl}-6-fluoro-3-biphenylyl)methyl]-3-[(1-methyl-4-piperidinyl)methyl]benzamide;

or a pharmaceutically acceptable salt, or non-salt form thereof.

The most preferred compounds are selected from the group consisting of:

N-[(6-fluoro-3'-{[(3S)-3-methyl-1-piperazinyl]methyl]-3-biphenylyl)methyl]-3-[(4-methyl-1-piperazinyl)methyl]benzamide tetra-trifluoroacetate;

3-[(4-methyl-1-piperazinyl)methyl]-N-{[3'-(1-piperazinylmethyl)-3-biphenylyl]methyl}benzamide tetra-trifluoroacetate;

N-({3'-[(1S,4S)-2,5-diazabicyclo[2.2.1]hept-2-ylmethyl]-3-biphenylyl}methyl)-3-[(4-methyl-1-piperazinyl)methyl]benzamide tetra-trifluoroacetate;

3-[(4-methyl-1-piperazinyl)methyl]-N-({3'-[(3-methyl-1-piperazinyl)methyl]-3-biphenylyl}methyl)benzamide tetra-trifluoroacetate;

N-[(6-(methyloxy)-3'-{[(3S)-3-methyl-1-piperazinyl]methyl}-3-biphenylyl)methyl]-3-[(4-methyl-1-piperazinyl)methyl]benzamide tetra-trifluoroacetate;

N-[(6-fluoro-3'-{[(3S)-3-methyl-1-piperazinyl]methyl}-3-biphenylyl)methyl]-3-(1-piperazinylmethyl)benzamide tetra-trifluoroacetate;

N-[(6-fluoro-3'-{[(3S)-3-methyl-1-piperazinyl]methyl}-3-biphenylyl)methyl]-3-(hexahydro-1H-1,4-diazepin-1-ylmethyl)benzamide tetra-trifluoroacetate;

3-[(1S,4S)-2,5-diazabicyclo[2.2.1]hept-2-ylmethyl]-N-[(6-fluoro-3'-{[(3S)-3-methyl-1-piperazinyl]methyl)-3-biphenylyl)methyl]benzamide tetra-trifluoroacetate;

N-[(6-fluoro-3'-{[(3S)-3-methyl-1-piperazinyl]methyl}-3-biphenylyl)methyl]-3-[(3-methyl-1-piperazinyl)methyl]benzamide tetra-trifluoroacetate;

3-{[4-(3-cyanopropyl)-1-piperazinyl]methyl}-N-[(6-fluoro-3'-{[(3S)-3-methyl-1-piperazinyl]methyl}-3-biphenylyl)methyl]benzamide tetra-trifluoroacetate;

4-{[3-({[(6-fluoro-3'-{[(3S)-3-methyl-1-piperazinyl]methyl}-3-biphenylyl)methyl]amino}carbonyl)phenyl]methyl}-2-piperazinecarboxamide tetra-trifluoroacetate;

N-[(6-fluoro-3'-{[(3S)-3-methyl-1-piperazinyl]methyl)-3-biphenylyl)methyl]-3-({4-[3-(methyloxy)propyl]-1-piperazinyl)methyl)benzamide tetra trifluoroacetate;

N-[(6-fluoro-3'-{[(3S)-3-methyl-1-piperazinyl]methyl}-3-biphenylyl)methyl]-3-[(4-methyl-1-piperidinyl)methyl]benzamide tri-trifluoroacetate;

N-[(6-fluoro-3'-{[(3S)-3-methyl-1-piperazinyl]methyl)-3-biphenylyl)methyl]-3-({4-[2-(phenyloxy)ethyl]-1-piperazinyl)methyl)benzamide tetra-trifluoroacetate;

N-[(6-fluoro-3'-{[(3S)-3-methyl-1-piperazinyl]methyl}-3-biphenylyl)methyl]-3-{[4-(3-hydroxypropyl)-1-piperazinyl]methyl}benzamide tetra-trifluoroacetate;

3-({2-[(dimethylamino)methyl]-1-piperidinyl}methyl)-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl]-3-biphenylyl)methyl]-3-(4-morpholinylmethyl)benzamide tri-trifluoroacetate;

3-[(2,5-dimethyl-1-piperazinyl)methyl]-N-[(6-fluoro-3'-{[(3S)-3-methyl-1-piperazinyl]methyl)-3-biphenylyl)methyl]benzamide tetra-trifluoroacetate;

N-[(6-fluoro-3'-{[(3S)-3-methyl-1-piperazinyl]methyl}-3-biphenylyl)methyl]-3-{[(1S,4S)-5-methyl-2,5-diazabicyclo[2.2.1]hept-2-yl]methyl}benzamide tetra-trifluoroacetate;

N-[(6-fluoro-3'-{[(3S)-3-methyl-1-piperazinyl]methyl}-3-biphenylyl)methyl]-3-[(4-formyl-1-piperazinyl)methyl]benzamide tri-trifluoroacetate;

3-{[[3-(dimethylamino)propyl](methyl)amino]methyl}-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl)-3-biphenylyl)methyl]-3-{[4-(1-methyl-4-piperidinyl)-1-piperazinyl]methyl}benzamide penta-trifluoroacetate;

3-{[[2-(dimethylamino)ethyl](methyl)amino]methyl}-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[(2E)-3-phenyl-2-propen-1-yl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-[(4-methylhexahydro-1H-1,4-diazepin-1-yl)methyl]benzamide tetra-trifluoroacetate;

3-[(dimethylamino)methyl]-N-[(6-fluoro-3'-{[(3S)-3-methyl-1-piperazinyl]methyl}-3-biphenylyl)methyl]benzamide tri-trifluoroacetate;

N-[(6-fluoro-3'-{[(3S)-3-methyl-1-piperazinyl]methyl}-3-biphenylyl)methyl]-3-({4-[2-(4-morpholinyl)ethyl]-1-piperazinyl}methyl)benzamide penta-trifluoroacetate;

3-[(diethylamino)methyl]-N-[(6-fluoro-3'-{[(3S)-3-methyl-1-piperazinyl]methyl}-3-biphenylyl)methyl]benzamide tri-trifluoroacetate;

3-({4-[2-(dimethylamino)ethyl]-1-piperidinyl}methyl)-N-[(6-fluoro-3'-{[(3S)-3-methyl-1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[2-(1-pyrrolidinyl)ethyl]-1-piperazinyl}methyl)benzamide penta-trifluoroacetate;

N-[(6-fluoro-3'-{[(3S)-3-methyl-1-piperazinyl]methyl}-3-biphenylyl)methyl]-3-{[methyl(1-methyl-3-pyrrolidinyl)amino]methyl}benzamide tetra-trifluoroacetate;

N-[(6-fluoro-3'-{[(3S)-3-methyl-1-piperazinyl]methyl}-3-biphenylyl)methyl]-3-(1-piperidinylmethyl)benzamide tri-trifluoroacetate;

N-[(6-fluoro-3'-{[(3S)-3-methyl-1-piperazinyl]methyl}-3-biphenylyl)methyl]-3-[(1-methyl-1,7-diazaspiro[4.4]non-7-yl)methyl]benzamide tetra-trifluoroacetate;

N-[(6-fluoro-3'-{[(3S)-3-methyl-1-piperazinyl]methyl}-3-biphenylyl)methyl]-3-(4-piperidinylmethyl)benzamide;

N-[(3'-{[(3S)-3-methyl-1-piperazinyl]methyl}-3-biphenylyl)methyl]-3-(4-piperidinylmethyl)benzamide;

N-{[3'-(1-piperazinylmethyl)-3-biphenylyl]methyl}-3-(3-pyridinyl)benzamide;

N-[(6-fluoro-3'-{[(3S)-3-methyl-1-piperazinyl]methyl}-3-biphenylyl)methyl]-3-[(1-methyl-4-piperidinyl)methyl]benzamide trifluoroacetate;

N-{[6-fluoro-3'-(1-piperazinylmethyl)-3-biphenylyl]methyl}-3-(4-piperidinylmethyl)benzamide;

N-[(4-fluoro-3'-{[(3S)-3-methyl-1-piperazinyl]methyl}-3-biphenylyl)methyl]-3-(4-piperidinylmethyl)benzamide;

N-[(6-fluoro-3'-[[(3S)-3-methyl-1-piperazinyl]methyl}-3-biphenylyl)methyl]-4-(4-piperidinylmethyl)benzamide trifluoroacetate;

N-{[3-(6-{[(3S)-3-methyl-1-piperazinyl]methyl}-2-pyridinyl)phenyl]methyl}-3-(4-piperidinylmethyl)benzamide trifluoroacetate; and N-[(6-fluoro-3'-{[(3S)-3-methyl-1-piperazinyl]methyl}-3-biphenylyl)methyl]-N-(2-{[2-(methyloxy)ethyl]oxy}ethyl)-3-(4-piperidinylmethyl)benzamide;

or a pharmaceutically acceptable salt, or non-salt form thereof.

Methods of Preparation

Preparation

The compounds of Formula (I) may be obtained by applying synthetic procedures, some of which are illustrated in the Schemes below. The synthesis provided for these Schemes is applicable for producing compounds of Formula (I) having a variety of different R1, R2, R3, R4 and X, which are reacted, employing substituents which are suitably protected, to achieve compatibility with the reactions outlined herein. Subsequent deprotection, in those cases, then affords compounds of the nature generally disclosed. While some Schemes are shown with specific compounds, this is merely for illustration purpose only.

Preparation 1

As shown in Scheme 1, bromo benzylamines 1 were loaded onto 2,6-dimethoxy-4-polystyrenebenzyloxy-benzaldehyde (DMHB resin) via reductive amination. The resin-bound amines 2 were reacted with 3-formylbenzoic acid to yield amides 3, which were reductively aminated with various amines NHR1R2, to yield amines 4. Suzuki coupling of 4 with (3-formylphenyl)boronic acid gave biphenylaldehydes 5, which were then subject to reductive amination with amines NHR3R4, followed by cleavage, affording desired products 6.

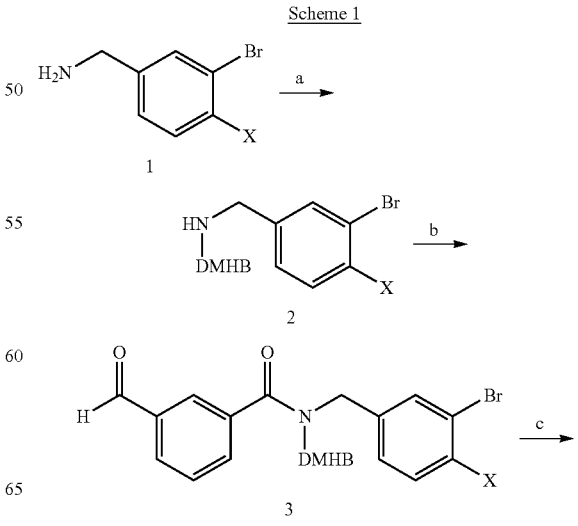

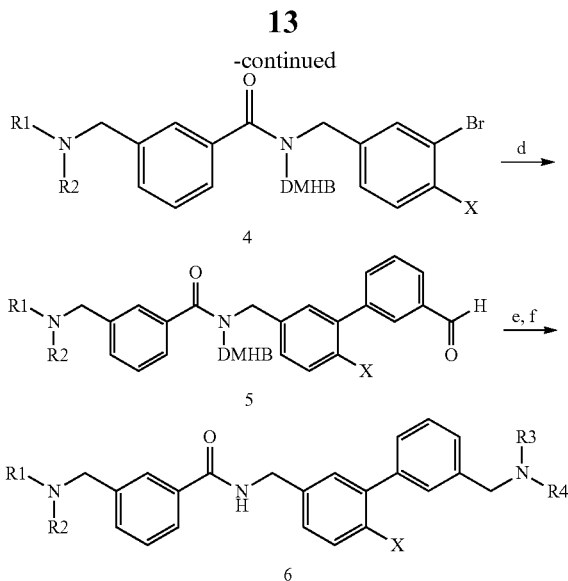

Conditions:
a) DMHB resin, Na(OAc)₃BH, acetic acid, 1-methyl-2-pyrrolidinone (NMP), rt;
b) 3-formylbenzoic acid, 1,3-diisopropylcarbodiimide (DIC), 1,2 dichloroethane (DCE): dimethylformamide (DMF) = 1:1, rt;
c) NHR1R2, Na(OAc)₃BH, Na₂SO₄, DCE, rt;
d) (3-formylphenyl)boronic acid, Pd(PPh₃)₄, Cs₂CO₃, dimethoxyethane (DME), 80° C.;
e) NHR3R4, Na(OAc)₃BH, Na₂SO₄, DCE, rt;
f) 50% of trifluoroacetic acid (TFA) in DCE, rt.

SYNTHETIC EXAMPLES

The invention will now be described by reference to the following Examples which are merely illustrative and are not to be construed as a limitation of the scope of the present invention. Most reagents and intermediates are commercially available or are prepared according to procedures in the literature. The preparation of intermediates not described in the literature is illustrated below.

Flash column chromatography was carried out using Merck 9385 silica unless stated otherwise.

LC/MS analyses were conducted under the following conditions:

Column: 3.3 cm × 4.6 mm ID, 3 um ABZ + PLUS
Flow Rate: 3 ml/min
Injection Volume: 5 μl
Temp: Room temperature
Solvents:  A: 0.1% Formic Acid + 10 mMolar Ammonium Acetate.
           B: 95% Acetonitrile + 0.05% Formic Acid
Gradient:

| Time | A % | B % |
|------|-----|-----|
| 0.00 | 100 | 0   |
| 0.70 | 100 | 0   |
| 4.20 | 0   | 100 |
| 5.30 | 0   | 100 |
| 5.50 | 100 | 0   |

The Mass Directed Automated Preparative (MDAP) was conducted under the conditions described in System A or in System B:
System A: Formate salts
  The preparative column used was a Supelcosil ABZplus (10 cm×2.12 cm internal diameter; particle size 5m)
  UV detection wavelength: 200-320 nM
  Flow rate: 20 ml/min
  Injection Volume: 0.5 ml
  Solvent A: 0.1% formic acid
  Solvent B: 95% acetonitrile+0.05% formic acid
System B TFA salts
  The preparative column used was a Supelcosil ABZplus (10 cm×2.12 cm internal diameter; particle size 5 m)
  UV detection wavelength: 200-320 nM
  Flow rate: 20 m/min
  Injection Volume: 0.5 ml
  Solvent A: water+0.1% trifluoroacetic acid
  Solvent B: acetonitrile+0.1% trifluoroacetic acid
  The Gilson preparatory HPLC was conducted under the following conditions:
  Column: 75×33 mm I. D., S-5 um, 12 nm
  Flow rate: 30 mL/min
  Injection Volume: 0.800 mL
  Room temperature
  Solvent A: 0.1% trifluoroacetic acid in water
  Solvent B: 0.1% trifluoroacetic acid in acetonitrile

Example 1

Preparation of N-[(6-fluoro-3'-{[(3S)-3-methyl-1-piperazinyl]methyl}-3-biphenylyl)methyl]-3-[(4-methyl-1-piperazinyl)methyl]benzamide tetra-trifluoroacetate a) DMHB resin bound 3-bromo-4-fluoro-benzylamine To a mixture of DMHB resin (10 g, 1.5 mmol/g loading, 15 mmol) in N-methyl pyrrolidine (NMP, 150 mL), was added 3-bromo-4-fluoro-benzylamine (15.5 g, 75 mmol), acetic acid (15 mL, 1% v/v), and sodium triacetoxyborohydride (19 g, 90 mmol). The mixture was shaken at rt for overnight and was then washed with NMP (200 mL×2), dichloromethane (DCM) (200 mL×2), MeOH (200 mL×2) and DCM (200 mL×2). The resulting resin was dried in vacuum oven at 20° C. for overnight to yield DMHB resin bound 3-bromo-4-fluoro-benzylamine (15 mmol).

b) DMHB resin-bound N-[(3-bromo-4-fluorophenyl)methyl]-3-formylbenzamide

To a mixture of above resin-bound 3-bromo-4-fluoro-benzylamine (200 mg, 1.15 mmol/g (theoretical loading), 0.23 mmol) in DCE/DMF (1:1, 8 mL) was added 3-formylbenzoic acid (350 mg, 2.3 mmol) and DIC (0.36 mL, 2.3 mmol). The mixture was shaken at rt for overnight and was then washed with DMF (20 mL×2), DCM (20 mL×2), MeOH (20 mL×2) and DCM (20 mL×2). The resulting resin was dried in vacuum oven at 20° C. for overnight to yield DMHB resin-bound N-[(3-bromo-4-fluorophenyl)methyl]-3-formylbenzamide (0.23 mmol). An analytical amount of the resin was cleaved with 50% of TFA in DCE for 10 min. The resulting solution was concentrated in vacuo and dissolved in 0.5 mL of CH₃CN. MS (ESI): 336 [M+H]⁺.

c) DMHB resin-bound N-[(3-bromo-4-fluorophenyl)methyl]-3-[(4-methyl-1-piperazinyl)methyl]benzamide To a mixture of DMHB resin-bound bound N-[(3-bromo-4-fluorophenyl)methyl]-3-formylbenzamide (200 mg, 0.99 mmol/g, 0.198 mmol) in 10 mL of DCE was added Na₂SO₄ (0.141 g, 0.99 mmol) and 1-methylpiperazine (0.1 g, 0.99 mmol). After shaking for 10 min, Na(OAc)₃BH (0.252 g, 1.19 mmol) was added. After being shaken at rt for overnight, the resin was washed with tetrahydrofuran (THF) (20 mL×2), THF:H$_2$O (1:1, 20 mL×2), H$_2$O (20 mL×2), THF:H$_2$O (1:1, 20 mL×2), THF (20 mL×2), DCM (20 mL×2) and dried in vacuum oven at 20° C. for overnight to yield DMHB resin-bound N-[(3-bromo-4-fluorophenyl)methyl]-3-[(4-methyl-1-piperazinyl)methyl]benzamide (0.198 mmol). An analytical amount of the resin was cleaved with 50% of TFA in DCE for 10 min. The resulting solution was concentrated in vacuo and dissolved in 0.5 mL of CH$_3$CN. MS (ESI): 420 [M+H]$^+$.

d) DMHB resin-bound N-[(6-fluoro-3'-formyl-3-biphenylyl)methyl]-3-[(4-methyl-1-piperazinyl)methyl]benzamide To a mixture of DMHB resin-bound N-[(3-bromo-4-fluorophenyl)methyl]-3-[(4-methyl-1-piperazinyl)methyl]benzamide (200 mg, 0.92 mmol/g, 0.184 mmol) in 5 mL DME was added 3-formylphenyl boronic acid (83 mg, 0.55 mmol), 2 M Cs$_2$CO$_3$ aqueous solution (0.275 mL, 0.55 mmol), and Pd(PPh$_3$)$_4$ (43 mg, 0.0368 mmol). After being purged with argon for 5-10 min, the mixture was heated at 80° C. under argon for 16 h. The resulting resin was washed with THF (20 mL×2), THF:H$_2$O (1:1, 20 mL×2), H$_2$O (20 mL×2), THF:H$_2$O (1:1, 20 mL×2), THF (20 mL×2), DCM (20 mL×2), and dried in vacuum oven at 20° C. for overnight to yield DMHB resin-bound N-[(6-fluoro-3'-formyl-3-biphenylyl)methyl]-3-[(4-methyl-1-piperazinyl)methyl]benzamide (0.184 mmol). An analytical amount of the resin was cleaved with 50% of TFA in DCM for 10 min. The resulting solution was concentrated in vacuo and dissolved in 0.5 mL of CH$_3$CN. MS (ESI): 446 [M+H]$^+$.

e,f) N-[(6-fluoro-3'-{[(3S)-3-methyl-1-piperazinyl]methyl}-3-biphenylyl)methyl]-3-[(4-methyl-1-piperazinyl)methyl]benzamide To a mixture of DMHB resin-bound N-[(6-fluoro-3'-formyl-3-biphenylyl)methyl]-3-[(4-methyl-1-piperazinyl)methyl]benzamide (200 mg, 0.92 mmol/g, 0.184 mmol) in 17 mL of DCE was added Na$_2$SO$_4$ (0.24 g, 1.7 mmol) (S)-2-methylpiperazine (0.32 g, 1.7 mmol). After shaking for 10 min, Na(OAc)$_3$BH (0.43 g, 2.04 mmol) was added. After being shaken at rt for overnight, the resin was washed with THF (20 mL×2), THF:H$_2$O (1:1, 20 mL×2), H$_2$O (20 mL×2), THF:H$_2$O (1:1, 20 mL×2), THF (20 mL×2), DCM (20 mL×2) and dried in vacuum oven at 20° C. for overnight. The resulting resin was cleaved with 5 mL of 50% of TFA in DCE for 30 min and treated again with 5 mL of 50% of TFA in DCE for 30 min. The combined cleavage solution was concentrated in vacuo. The residue was dissolved in DMSO and purified using a Gilson semi-preparative HPLC system with a YMC ODS-A (C-18) column 50 mm by 30 mm ID, eluting with 10% B to 90% B in 3.2 min, hold for 1 min where A=H$_2$O (0.1% trifluoroacetic acid) and B=CH$_3$CN (0.1% trifluoroacetic acid) pumped at 25 mL/min, to produce N-[(6-fluoro-3'-{[(3S)-3-methyl-1-piperazinyl]methyl}-3-biphenylyl)methyl]-3-[(4-methyl-1-piperazinyl)methyl]benzamide as a tetra-trifluoroacetate salt (white powder, 153 mg, 52% over 4 steps). MS (ESI): 530 [M+H]$^+$.

Proceeding in a similar manner, but replacing 1-methylpiperazine with the appropriate amines, and/or replacing (S)-2-methylpiperazine with the appropriate amines, and/or replacing 3-bromo-4-fluoro-benzylamine with appropriate bromobenzylamines, the compounds listed in Table 1 were prepared.

In the case of examples 6, 7, and 8, the amine used in step c) was a mono t-butoxy carbonyl (BOC) protected amine. The BOC group was later removed during step t).

In the case of examples 2 and 3 the amine used in step e) was a BOC protected amine. The BOC group being later removed during step f).

TABLE 1

| Example | Compound | MS [M + H]$^+$ |
|---|---|---|
| 2 | | 498 |
| 3 | | 510 |
| 4 | | 512 |

TABLE 1-continued

| Example | Compound | MS [M + H]+ |
|---------|----------|-------------|
| 5 | | 542 |
| 6 | | 516 |
| 7 | | 530 |
| 8 | | 528 |
| 9 | | 530 |
| 10 | | 583 |
| 11 | | 559 |
| 12 | | 588 |

TABLE 1-continued

| Example | Compound | MS [M + H]+ |
|---|---|---|
| 13 | | 529 |
| 14 | | 636 |
| 15 | | 574 |
| 16 | | 572 |
| 17 | | 517 |
| 18 | | 544 |
| 19 | | 542 |

TABLE 1-continued

| Example | Compound | MS [M + H]+ |
|---|---|---|
| 20 | | 544 |
| 21 | | 546 |
| 22 | | 613 |
| 23 | | 532 |
| 24 | | 632 |
| 25 | | 544 |
| 26 | | 475 |

TABLE 1-continued

| Example | Compound | MS [M + H]+ |
|---|---|---|
| 27 | | 629 |
| 28 | | 503 |
| 29 | | 586 |
| 30 | | 613 |
| 31 | | 544 |
| 32 | | 515 |
| 33 | | 570 |

TABLE 1-continued

| Example | Compound | MS [M + H]+ |
|---|---|---|
| 34 | 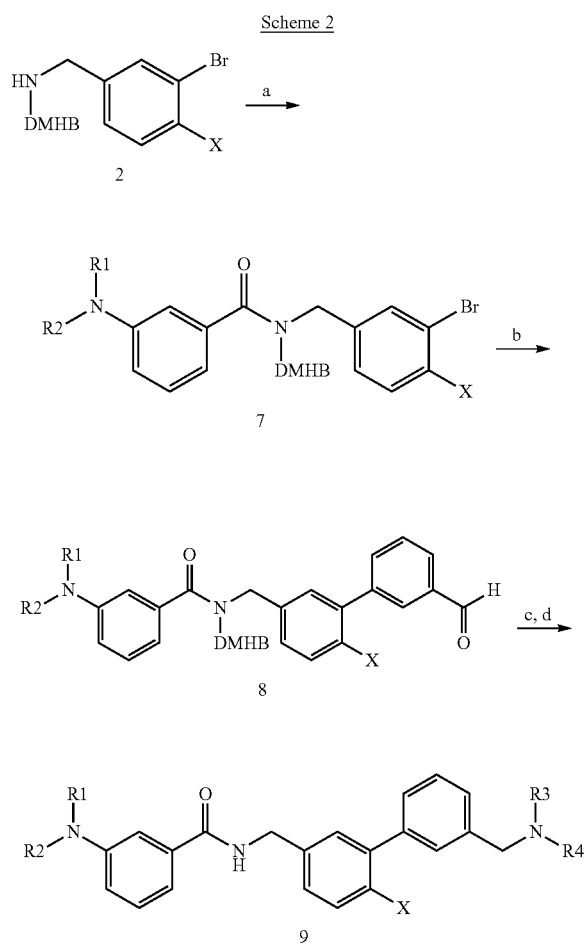 | 627 |

Preparation 2

As shown in scheme 2, the resin-bound bromobenzylamines 2 were reacted with various 3-substituted benzoic acids to yield amides 7, which underwent Suzuki coupling with (3-formylphenyl)boronic acid to give biphenylaldehydes 8. Reductive amination of 8 with amines NHR3R4, followed by cleavage, afforded desired products 9.

Scheme 2

Conditions:
a) various 3-substituted benzoic acids, DIC, DCE: DMF = 1:1, rt;
b) (3-formylphenyl)boronic acid, Pd(PPh3)4, Cs2CO3, DME, 80° C.;
c) NHR3R4, Na(OAc)3BH, Na2SO4, DCE, rt;
d) 50% of TFA in DCE, rt.

Example 35

Preparation of 3-(dimethylamino)-N-({3'-[(3-methyl-1-piperazinyl)methyl]-3-biphenylyl}methyl)benzamide tri-trifluoroacetate a) DMHB resin-bound N-[(3-bromophenyl)methyl]-3-(dimethylamino)benzamide To a 250 mL shaker vessel was added 2,6-dimethoxy-4-polystyrenebenzyloxy-benzaldehyde (DMHB resin) (10 g, 1.5 mmol/g, 15 mmol) and 150 mL of 1-methyl-2-pyrrolidinone (NMP). 3-Bromo-benzylamine HCl salt (17 g, 75 mmol), diisopropylethylamine (DIEA) (13 mL, 75 mmol), acetic acid (HOAc) (15 mL), and Na(OAc)3BH (19.1 g, 90 mmol) were then added. The resulting mixture was shaken at rt for overnight, and was then washed with NMP (150 mL×2), dichloromethane (DCM) (150 mL×2), MeOH (150 mL×2) and DCM (150 mL×2). The resulting resin was dried in vacuum oven at 35° C. for overnight to yield DMHB resin-bound 3-bromo-benzylamine (15 mmol).

To a mixture of DMHB resin-bound 3-bromo-benzylamine (2 g, 1.2 mmol/g (theoretical loading), 2.4 mmol) in DCE/DMF (1:1, 80 mL) was added 3-(dimethylamino)benzoic acid (4.0 g, 24 mmol) and DIC (3.7 mL, 24 mmol). The mixture was shaken at rt for overnight and was then washed with DMF (100 mL×2), DCM (100 mL×2), MeOH (100 mL×2) and DCM (100 mL×2). The resulting resin was dried in vacuum oven at 35° C. for overnight to yield DMHB resin-bound N-[(3-bromophenyl)methyl]-3-(dimethylamino)benzamide (2.4 mmol). An analytical amount of the resin was cleaved with 20% of TFA in DCE for 10 min. The resulting solution was concentrated in vacuo and dissolved in 0.5 mL of MeOH. MS (ESI): 334 [M+H]+.

b) DMHB resin-bound 3-(dimethylamino)-N-[(3'-formyl-3-biphenylyl)methyl]benzamide To a mixture of DMHB resin-DMHB resin-bound N-[(3-bromophenyl)methyl]-3-(dimethylamino)benzamide (3.03 g, 1.0 mmol/g (theoretical loading), 3.03 mmol) in 76 mL of DME was added 3-formylphenyl boronic acid (1.36 g, 9.09 mmol), 2 M K2CO3 aqueous solution (4.5 mL, 9.09 mmol), and Pd(PPh3)4 (0.18 g, 0.15 mmol). After purged with argon for 5-10 min, the mixture was heated at 80° C. under argon for 10 h. The resulting resin was washed with THF (100 mL×2), THF:H2O (1:1, 100 mL×2), H2O (100 mL×2), THF:H2O (1:1, 100 mL×2), THF (100 mL×2), DCM (100 mL ×2), and dried in vacuum oven at 35° C. for overnight to yield DMHB resin-bound 3-(dimethylamino)-N-[(3'-formyl-3-biphenylyl)methyl]benzamide (3.03 mmol). An analytical amount of the resin was cleaved with 20% of TFA in DCM for 10 min. The resulting solution was concentrated in vacuo and dissolved in 0.5 mL of CH₃CN. MS (ESI): 359 [M+H]⁺.

c,d) 3-(dimethylamino)-N-({3'-[(3-methyl-1-piperazinyl)methyl]-3-biphenylyl}methyl)benzamide To a mixture of the above DMHB resin-bound 3-(dimethylamino)-N-[(3'-formyl-3-biphenylyl)methyl]benzamide (50 mg, 0.99 mmol/g (theoretical loading), 0.0495 mmol) in 2 mL of DCE was added Na₂SO₄ (60 mg, 0.42 mmol) and 2-methylpiperazine (42 mg, 0.42 mmol). After shaking for 10 min, Na(OAc)₃BH (98 mg, 0.46 mmol) was added. After shaken at rt for overnight, the resin was washed with THF (10 mL×2), THF:H₂O (1:1, 10 mL×2), H₂O (10 mL×2), THF:H₂O (1:1, 10 mL×2), THF (10 mL×2), DCM (10 mL×2) and dried in vacuum oven at 35° C. for overnight. The resulting resin was cleaved with 2 mL of 20% of TFA in DCE for 30 min and treated again with 2 mL of 20% of TFA in DCE for 30 min. The combined cleavage solution was concentrated in vacuo. The residue was dissolved in DMSO and purified using a Gilson semi-preparative HPLC system with a YMC ODS-A (C-18) column 50 mm by 20 mm ID, eluting with 10% B to 90% B in 3.2 min, hold for 1 min where A=H₂O (0.1% trifluoroacetic acid) and B=CH₃CN (0.1% trifluoroacetic acid) pumped at 25 mL/min, to produce 3-(dimethylamino)-N-({3'-[(3-methyl-1-piperazinyl)methyl]-3-biphenylyl}methyl)benzamide as a tri-trifluoroacetate salt (White powder, 20 mg, 50% over 4 steps). MS (ESI): 443 [M+H]⁺.

Proceeding in a similar manner, but replacing 3-(dimethylamino)benzoic acid with the appropriate benzoic acids, and/or replacing 2-methylpiperazine with the appropriate amines, the compounds listed in Table 2 were prepared.

In the case of examples 36, 37, 38, and 39, the amine used in the step c) was a BOC protected amine, the BOC group was later removed in the step d).

TABLE 2

| Example | Compound | MS [M + H]⁺ |
|---------|----------|-------------|
| 36 | | 429 |
| 37 | | 441 |
| 38 | | 401 |
| 39 | | 413 |

Preparation 3

The compounds of general structure 17 were prepared in solution phase following the route outlined in Scheme 3. Firstly, reductive amination of the benzaldehydes 11 with the N-protected piperazines 12 gave the tertiary amines 14. Coupling of 14 with the boronic acids 13 using the Suzuki reaction gave the biphenyl derivatives 15. Further reduction of the nitrile moiety with borane yielded the primary amines 16. Subsequent coupling of 16 to the appropriate benzoic acids followed by deprotection of the piperazine nitrogen gave the corresponding products 17.

hexanes, 40 mmol) at rt. The solution was stirred for 30 min before TBDMSCI (3.04 g, 20 mmol) was added. The mixture was stirred for an additional hour and $(Boc)_2O$ (5.2 g, 24 mmol) was added to the solution. The resulting mixture was stirred for another hour and diluted with $H_2O$ (50 mL). The organic layer was separated, washed with brine (50 mL), dried over $Na_2SO_4$ and concentrated under vacuum. Flash chromatography on silica (5% MeOH/2% $NH_4OH$/93% $CH_2Cl_2$) then provided the title compound as a yellow oil (3.7 g, 93%). LC/MS: m/z, 201(M+H); $^1$HNMR ($CDCl_3$) δ1.26

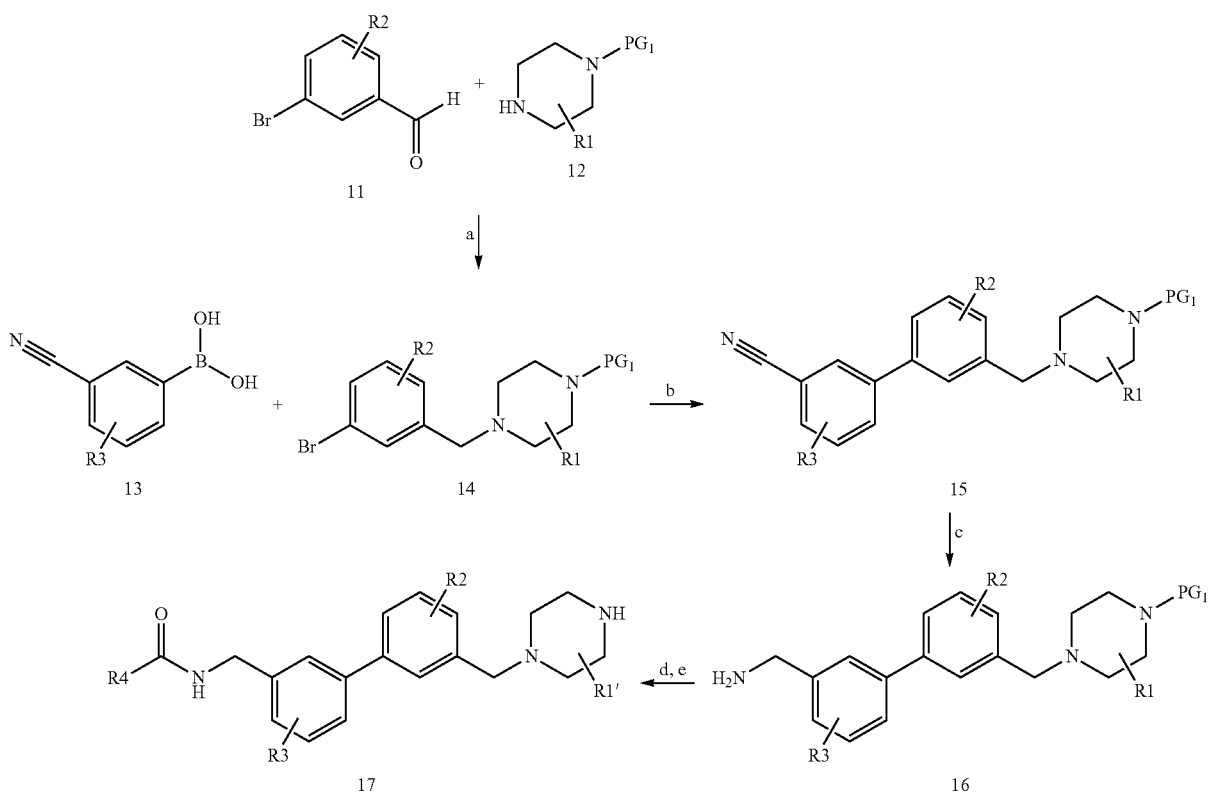

Scheme 3

Conditions:
a) NaB(OAc)$_3$H, DCM, rt;
b) Pd(PPh$_3$)$_4$, Na$_2$CO$_3$, DME, 78° C.;
c) BH$_3$, THF;
d) HATU, R$_4$CO$_2$H, DIPEA, DMF;
e) Deprotection of N-piperazine with HCl, TFA or H$_2$/Pd/C.

Intermediate 1

1,1-dimethylethyl (2S)-2-methyl-1-piperazinecarboxylate

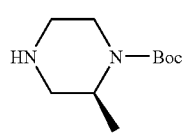

A solution of (S)-2-methyl piperazine (2 g, 20 mmol) in THF (200 mL) was mixed with nBuLi (25 mL, 1.6 M in (3H, d), 1.49 (9H, s), 2.1 (1H, s), 2.7 (1H, m), 2.85 (1H, m), 3.0 (3H, m), 3.8 (1H, m), 4.2 (1H, m).

Intermediate 2

1,1-dimethylethyl (2S)-4-[(3-bromophenyl)methyl]-2-methyl-1-piperazine carboxylate

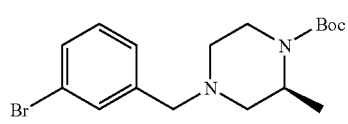

A solution of 1,1-dimethylethyl (2S)-2-methyl-1-piperazinecarboxylate (100 mg, 0.5 mmol) in CH$_2$Cl$_2$ (5 mL) was mixed with 3-bromo benzaldehyde (0.06 mL, 0.5 mmol) and NaB(OAc)$_3$H (0.16 g, 0.75 mmol). The resulting mixture was stirred for 12 hours, diluted with dichloromethane (30 mL) and washed with brine (50 mL). The organic layer was collected, dried over Na$_2$SO$_4$ and concentrated. Separation via a combiflash system then afforded the title compound (150 mg, 81%): LC/MS: m/z, 369 (M+H); $^1$HNMR (MeOD) δ 1.26 (3H, d), 1.47 (9H, s), 2.0 (1H, m), 2.1 (1H, m), 2.6 (1H, m), 2.8 (1H, m), 3.1 (1H, m), 3.3 (2H, s), 3.4 (1H, m), 3.5 (1H, m), 3.8 (1H, m), 4.2 (1H, m), 4.88 (1H, s), 7.25 (1H, m), 7.3 (1H, m), 7.4 (1H, m), 7.55 (1H, s).

Intermediate 3

1,1-Dimethylethyl (2S)-4-[(3'-cyano-4'-fluoro-3-biphenylyl)methyl]-2-methyl-1-piperazinecarboxylate

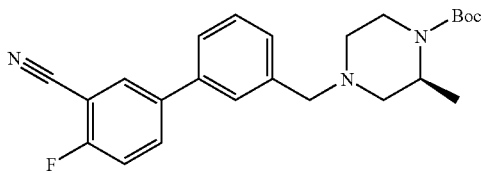

To a solution of (3-cyano-4-fluorophenyl)boronic acid (0.983 g, 5.96 mmol) in DME (40 mL) was added 1,1-dimethylethyl (2S)-4-[(3-bromophenyl)methyl]-2-methyl-1-piperazinecarboxylate (2.20 g, 5.96 mmol) followed by Na$_2$CO$_3$ (17 mL, 2M in H$_2$O, 34.0 mmol). The reaction vessel was flushed with Ar, and tetrakis(triphenylphosphine)palladium (0) (2.06 g, 1.78 mmol) was added. The reaction mixture was placed in an oil bath at 78° C. under Ar for overnight. The reaction was diluted with EtOAc (600 mL) and washed with H$_2$O (250 mL). The water layer was extracted with EtOAc (1×100 mL). The combined organic layers were dried over MgSO$_4$, filtered, and concentrated under vacuum. Purification of the crude residue by flash chromatography (20% EtOAc/80% hexane) on silica gel gave the title compound (1.77 g, 73.1%). EI-MS m/z 410 (M−H)$^+$.

Intermediate 4

1,1-Dimethylethyl (2S)-4-{[3'-(aminomethyl)-4'-fluoro-3-biphenylyl]methyl}-2-methyl-1-piperazinecarboxylate

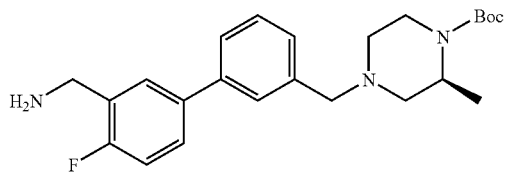

A solution of 1,1-dimethylethyl (2S)-4-[(3'-cyano-4'-fluoro-3-biphenylyl)methyl]-2-methyl-1-piperazinecarboxylate (2.29 g, 5.59 mmol) in THF (50 mL) was flushed with Ar. Borane (19 mL, 1M in THF, 19 mmol) was slowly added and the reaction was allowed to stir at room temperature for 12 hours. The reaction was quenched slowly with water, diluted with water (175 mL) and then extracted with EtOAc (2×250 mL). The combined organic layers were dried over MgSO$_4$, filtered, and concentrated under vacuum. The crude residue was placed onto a SPE silica cartridge (20 g) using 50% hexane/50% EtOAc, and then eluted with the following sequence: 50% hexane/50% EtOAc, 10% MeOH/90% DCM, 30% MeOH/70% DCM. The product fractions were combined and concentrated to give the title compound (1.48 g, 64.1%). EI-MS m/z 414(M−H)$^+$.

Intermediate 5

1,1-dimethylethyl 4-[(3-bromophenyl)methyl]-1-piperazinecarboxylate

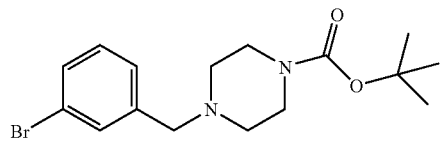

A solution of 3-bromobenzyl bromide (6 g) and Boc-piperazine (4.06 g) in acetonitrile (30 mL) was treated with triethylamine (3.36 mL). The resulting mixture was heated at reflux for 16 hours. After cooling to room temperature, the reaction mixture was treated with saturated sodium bicarbonate solution (20 mL), and then extracted with ethyl acetate (2×30 mL). The organic phases were combined, dried (MgSO$_4$) and concentrated under vacuum. The residue was purified by chromatography on silica (100 g) eluting with ethyl acetate/cyclohexane to give the title compound (6.95 g). LC/MS: m/z, 355, 357 (M+H), 2.40 min.

Intermediate 6

{3-[(4-{[(1,1-dimethylethyl)oxy]carbonyl}-1-piperazinyl)methyl]phenyl}boronic acid

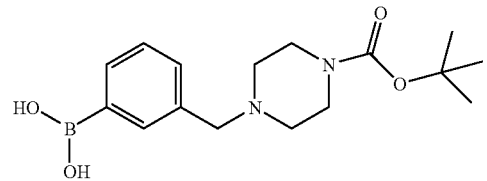

To a solution of 1,1-dimethylethyl 4-[(3-bromophenyl)methyl]-1-piperazinecarboxylate (6.55 g) in THF (20 mL) at −70° C. was added dropwise n-butyl lithium (15.4 mL, 2.5M solution in hexanes) over 10 minutes. After stirring for 30 mins at that temperature, the resulting orange solution was treated with trimethylborate (8.02 g). The reaction mixture was then allowed to warm up to room temperature and quenched with saturated ammonium chloride (15 mL). The solvent was removed under vacuum and the residue was partitioned between ethyl acetate (20 mL) and water (20 mL). The aqueous phase was separated and further extracted with ethyl acetate (20 mL). The organic phases were combined, dried (MgSO$_4$) and evaporated under vacuum to give the title compound (5 g) which was used directly for the preparation of 1,1-dimethylethyl 4-[(3'-cyano-3-biphenylyl)methyl]-1-piperazinecarboxylate without further purification. LC/MS: m/z, 321 (M+H), 1.91 min.

Intermediate 7

1,1-dimethylethyl 4-[(3'-cyano-3-biphenylyl)methyl]-1-piperazinecarboxylate

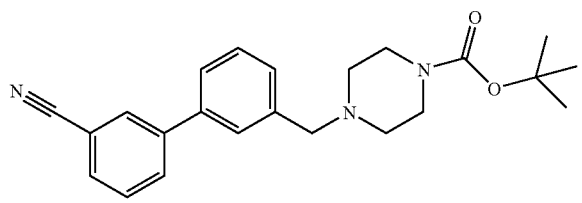

A mixture of {3-[(4-{[(1,1-dimethylethyl)oxy]carbonyl}-1-piperazinyl)methyl]phenyl}boronic acid (1 g), 3-bromobenzonitrile (0.56 g), potassium carbonate (1.725 g) and tetrakis triphenylphosphine palladium (180 mg) in dioxan/water (3:1, 4 mL) was sealed in a tube and heated at 150° C. for 15 minutes in a microwave vessel. After cooling to room temperature, the reaction mixture was then diluted with water (25 mL) and extracted with ethyl acetate (2×25 mL). The combined organic phases were dried (MgSO₄) and concentrated under vacuum. The resulting crude residue was further purified by flash column chromatography on silica (100 g) to give the title compound (0.9 g) (purity ca 75%). LC/MS: m/z, 378 (M+H), 2.57 min.

Intermediate 8

1,1-dimethylethyl 4-{[3'-(aminomethyl)-3-biphenylyl]methyl}-1-piperazinecarboxylate

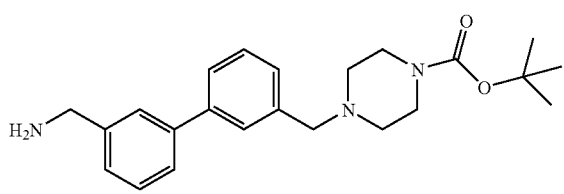

A solution of 1,1-dimethylethyl 4-[(3'-cyano-3-biphenylyl)methyl]-1-piperazinecarboxylate (4.5 g) in THF (30 mL) was treated with borane. THF (47.7 mL, 1M in THF) and the resulting mixture was heated at reflux for 1 hour. After cooling to room temperature, the reaction mixture was quenched with saturated ammonium chloride solution (20 mL) and extracted with ethyl acetate (3×30 mL). The combined organics were dried (MgSO₄), concentrated under vacuum to give a residue which was purified by flash chromatography on silica (100 g) to yield the title compound (1.1 g). LC/MS: m/z, 382 (M+H), 1.86 min.

Example 40

Preparation of N-[(4-fluoro-3'-{[(3S)-3-methyl-1-piperazinyl]methyl}-3-biphenylyl)methyl]-3-(4-piperidinylmethyl)benzamide

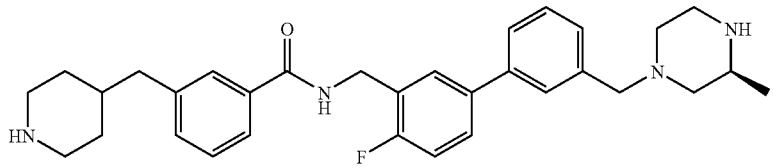

To a solution of 1,1-dimethylethyl (2S)-4-{[3'-(aminomethyl)-4'-fluoro-3-biphenylyl]methyl}-2-methyl-1-piperazinecarboxylate (0.108 g, 0.261 mmol) in DMF (2.5 mL) was added the commercially available 3-[(1-{[(1,1-dimethylethyl)oxy]carbonyl}-4-piperidinyl)methyl]benzoic acid (0.083 g, 0.261 mmol), HATU (0.110 g, 0.290 mmol), and diisopropylethylamine (0.10 mL, 0.574 mmol). The reaction was allowed to stir at room temperature for 2 days. The reaction was diluted with EtOAc (75 mL), washed with 1N HCl (2×20 mL), then saturated NaHCO₃ (3×20 mL), then brine (2×20 mL). The organic layer was dried over MgSO₄, filtered, and concentrated under vacuum. The residue was taken up in MeOH (4 mL) and HCl (4N in 1,2-dioxane, 2.5 mL) was added. The reaction was allowed to stir at room temperature overnight. The reaction was concentrated under vacuum, and the residue was taken up in 1 DMSO/1 MeOH and purified via MDAP (10-90% CH₃CN/H₂O/(0.1% TFA)). The desired fractions were isolated, and then taken up in DCM (8 mL) and 1N NaOH (8 mL) and allowed to stir for 1 hour. The DCM was isolated using a phase separator and then concentrated under vacuum to give the title compound (84.6 mg, 67.1%). El-MS m/z 515(M−H)⁺.

Example 41

Preparation of N-[(4-fluoro-3'-{[(3S)-3-methyl-1-piperazinyl]methyl}-3-biphenylyl)methyl]-3-(4-piperidinyl)benzamide

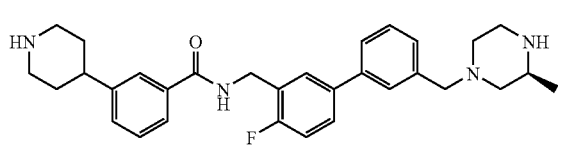

Following the procedure outlined in Example 40, 1,1-dimethylethyl (2S)-4-{[3'-(aminomethyl)-4'-fluoro-3-biphenylyl]methyl}-2-methyl-1-piperazinecarboxylate (0.100 g, 0.242 mmol), 3-(4-piperidinyl)benzoic acid (0.074 g, 0.243 mmol), HATU (0.103 g, 0.271 mmol), and diisopropylethylamine (0.10 mL, 0.574 mmol) in DMF (2.5 mL) were reacted to give the desired product (0.024 g, 21.0%). EI-MS m/z 501 (M−H)+.

Intermediate 9 phenylmethyl (2S)-4-[(3-bromophenyl)methyl]-2-methyl-1-piperazinecarboxylate

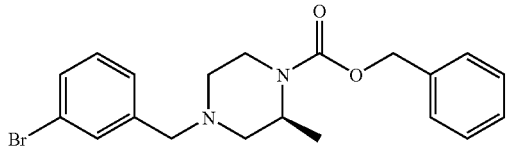

Preparation of (3S)-1-[(3-Bromophenyl)methyl]-3-methylpiperazine

Following the standard procedure outlined for intermediate 2, (2S)-1-piperazine (1.0 g, 10 mmol) was reacted with 3-bromobenzaldehyde (1.85 g, 10 mmol) to give (3S)-1-[(3-Bromophenyl)methyl]-3-methylpiperazine (2.0 g, 40%). LC/MS: m/z, 269 (M+H), 1.28 min.

Preparation of phenylmethyl (2S)-4-[(3-bromophenyl)methyl]-2-methyl-1-piperazinecarboxylate To a solution of (3S)-1-[(3-Bromophenyl)methyl]-3-methylpiperazine (250 mg, 0.5 mmol), TEA (0.5 ml, 3.5 mmol), and DMAP (12 mg, 0.1 mmol) in 1 mL of dry DMSO was added dropwise benzyl chloroformate (0.34 mL, 2.25 mmol) at 10° C. while stirring. The mixture was then heated and stirred at 50° C. for 1.5 h. After cooling to room temperature, 15 mL of ethyl acetate and 5 mL of saturated NaHCO₃ were added. The organic layer was separated, concentrated under vacuum and purified by Gilson reverse phase HPLC, eluting with acetonitrile/water/0.1% TFA (10/90 to 70/30, v/v, over 12 min), to give the title compound (180 mg, 70%). LC/MS: m/z, 403 (M+H), 1.74 min.

Intermediate 10

Phenylmethyl (2S)-4-[(5'-cyano-2'-fluoro-3-biphenylyl)methyl]-2-methyl-1-piperazinecarboxylate

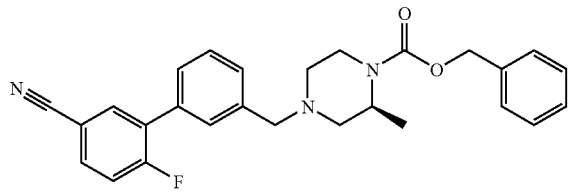

To the solution of (5-cyano-2-fluorophenyl)boronic acid (660 mg, 4 mmol) in dioxane/H₂O (40 mL/13.3 mL) was added phenylmethyl (2S)-4-[(3-bromophenyl)methyl]-2-methyl-1-piperazinecarboxylate (1.2 g, 4 mmol), K₂CO₃ (2.2 g mg, 16 mmol) and Pd(PPh₃)₄ (230 mg, 0.2 mmol). The resulting solution was irradiated in a microwave reactor at 150° C. for 20 minutes then diluted with EtOAc (5 mL). The organic layer was collected and the aqueous layer was extracted with EtOAc (2×5 mL). The organic layers were combined, dried over Na₂SO₄, filtered and concentrated. The residue was purified by Gilson HPLC, eluting with acetonitrile/water/0.1% TFA (10/90 to 90/10, v/v, over 12 min), to give the title compound (708 mg, 92%). LC/MS: m/z, 444 (M+H), 1.93 min.

Intermediate 11

Phenylmethyl (2S)-4-{[5'-(aminomethyl)-2'-fluoro-3-biphenylyl]methyl}-2-methyl-1-piperazinecarboxylate

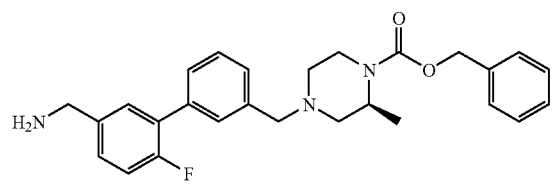

A solution of phenylmethyl (2S)-4-[(5'-cyano-2'-fluoro-3-biphenylyl)methyl]-2-methyl-1-piperazinecarboxylate (708 mg, 1.60 mmol) in THF (10 mL) was flushed with Ar. for 15 minutes. Borane (5.6 mL of a 1M solution in THF, 5.6 mmol) was slowly added and the reaction was allowed to stir at room temperature for 12 hours. The reaction was quenched slowly with 1N HCl (1 mL) and allowed to stir for 2 hours at rt. After neutralization to pH>10 with 2N NaOH, the reaction mixture was extracted with EtOAc (2×15 mL). The combined organic layers were dried over MgSO₄, filtered, and concentrated under vacuum. The crude residue was placed onto a aminopropyl SPE silica cartridge (10 g) and eluted with the following sequence: 50% hexane/50% EtOAc (3×20 mL), 10% MeOH/90% DCM (3×20 mL). The methanol fractions were combined and concentrated to give the title compound (660 mg, 92%). LC/MS: m/z, 448 (M+H), 1.63 min.

Intermediate 12

Phenylmethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate

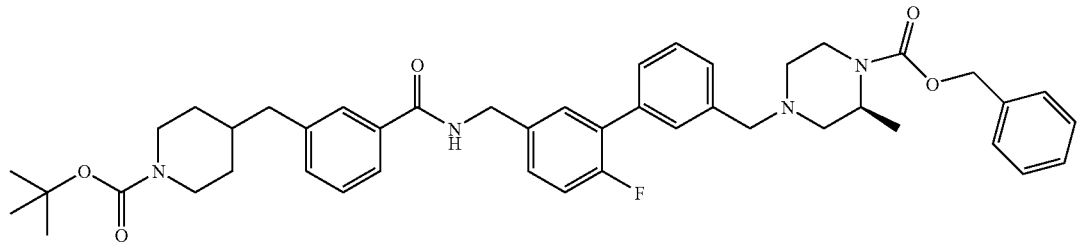

To a solution of 3-[(1-{[(1,1-dimethylethyl)oxy]carbonyl}-4-piperidinyl)methyl]benzoic acid (108 mg, 0.34 mmol) in dry DMF (2 mL) was added phenylmethyl (2S)-4-{[5'-(aminomethyl)-2'-fluoro-3-biphenylyl]methyl}-2-methyl-1-piperazinecarboxylate (150 mg, 0.334 mmol), DIPEA (0.1 mL, 0.7 mmol), HATU (142 mg, 0.37 mmol) and HOBt (150 mg, 1.1 mmol). The reaction mixture was stirred at room temperature for 2 h, followed by addition of saturated aq. Na$_2$CO$_3$ (1 mL) and EtOAc (5 mL). The organic layer was separated, dried over Na$_2$SO$_4$, and filtered. The filtrate was concentrated and the residue was purified on a 5 g amminopropyl SPE cartridge, eluting with DCM (3×5 mL), EtOAc (3×5 mL), and MeOH (3×5 mL). The product was recovered after evaporation of the DCM fractions (130 mg, 80%). LC/MS: m/z, 749 (M+H), 2.32 min.

Intermediate 13

1,1-Dimethylethyl 4-{[3-({[(6-fluoro-3'-{[(3S)-3-methyl-1-piperazinyl]methyl}-3-biphenylyl)methyl]amino}carbonyl)phenyl]methyl}-1-piperidinecarboxylate

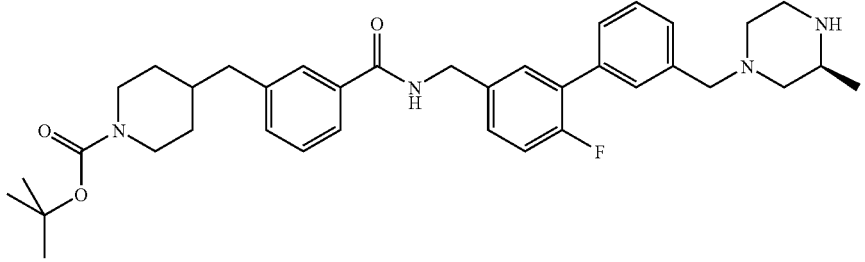

A solution of phenylmethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (1.5 g, 2.0 mmol) and 10% Pd/C (450 mg) in methanol (50 mL) was allowed to react with H$_2$ at rt under atmospheric pressure for 12 hours. The solvent was removed under vacuum. The resulting residue was purified by loading onto 20 g aminopropyl SPE cartridge and eluting sequentially with DCM (3×50 mL), EtOAc (3×50 mL), and MeOH (3×50 mL). The methanol fractions were combined and evaporated to give the title compound as a pale yellow solid (60 mg, 35%). LC/MS: m/z, 615 (M+H), 1.93 min.

Intermediate 14

1,1-dimethylethyl 4-{[3-({[(3'-{[(3S)-3,4-dimethyl-1-piperazinyl]methyl}-6-fluoro-3-biphenylyl)methyl]amino}carbonyl)phenyl]methyl}-1-piperidinecarboxylate

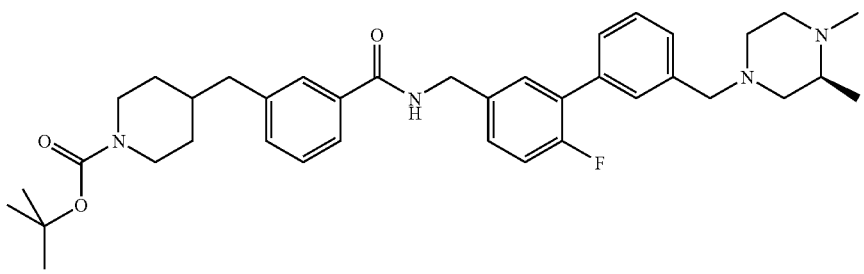

To a solution of 1,1-dimethylethyl 4-{[3-({[(6-fluoro-3'-{[(3S)-3-methyl-1-piperazinyl]methyl}-3-biphenylyl)-methyl]amino}carbonyl)phenyl]methyl}-1-piperidinecarboxylate (130 mg, 0.21 mmol) in MeOH (5 mL) was added formaldehyde (37% in water, 69 mg, 0.85 mmol). After 30 minutes stirring at rt, sodium borohydride (16 mg, 0.42 mmol) was added. After stirring at rt for additional 3 hours, the solvent was removed to give a residue which was purified by loading onto a 2 g aminopropyl SPE cartridge and eluting sequentially with DCM (3×5 mL), EtOAc (3×5 mL), and MeOH (3×5 mL). The dichloromethane and ethyl acetate fractions were combined and evaporated to give the title compound (130 mg, 99%). LC/MS: m/z, 629 (M+H), 1.97 min.

Example 42

Phenylmethyl (2S)-4-({2'-fluoro-5'-[({[3-(4-piperidinylmethyl)phenyl]carbonyl}amino)methyl]-3-biphenylyl}methyl)-2-methyl-1-piperazinecarboxylate

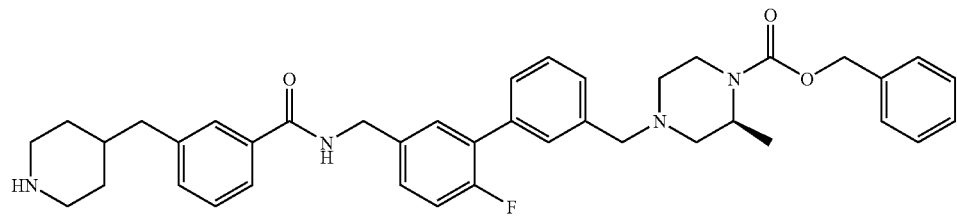

To a solution of phenylmethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (673 mg, 0.90 mmol) in 5 mL of 1,4-dioxane was added 5 mL of 4M HCl in 1,4-dioxane. The mixture was stirred at room temperature for 30 min. After removal of the solvent, the crude was purified by Gilson reverse phase HPLC, eluting with acetonitrile/water/0.1% TFA (10/90 to 70/30, v/v, over 12 min), to give the title compound (390 mg, 67%). LC/MS: m/z, 649 (M+H), 1.69 min.

Example 43

Phenylmethyl (2S)-4-[(2'-fluoro-5'-{([3-[(1-methyl-4-piperidinyl)methyl]phenyl}carbonyl)amino]methyl}-3-biphenylyl)methyl]-2-methyl-1-piperazinecarboxylate

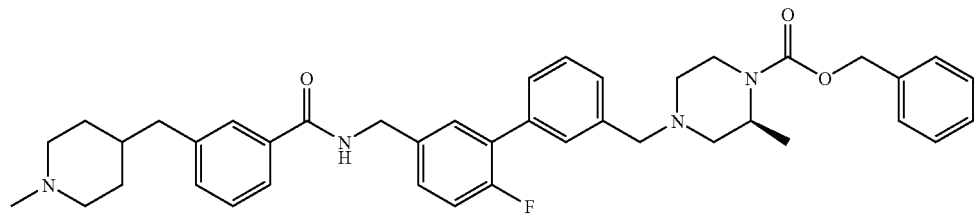

To a solution of phenylmethyl (2S)-4-({2'-fluoro-5'-[({[3-(4-piperidinyl)phenyl]carbonyl}amino)methyl]-3-biphenylyl}methyl)-2-methyl-1-piperazinecarboxylate in 5 mL of MeOH, was added dropwise formaldehyde (37%, 170 mg, 2.04 mmol). The mixture was stirred for 12 hours, the solvent was removed under vacuum, and the residue was purified on a 2 g aminopropyl SPE cartridge, eluting with DCM (3×5 mL), EtOAc (3×5 mL), and MeOH (3×5 mL). The EtOAc fractions were combined ad evaporated to give the title compound (240 mg, 71%). LC/MS: m/z, 663 (M+H), 2.02 min.

Example 44

N-[(6-fluoro-3'-{[(3S)-3-methyl-1-piperazinyl]methyl}-3-biphenylyl)methyl]-3-[(1-methyl-4-piperidinyl)methyl]benzamide

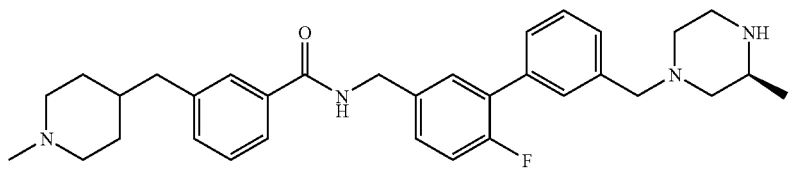

To a solution of phenylmethyl (2S)-4-[(2'-fluoro-5'-{[({3-[(1-methyl-4-piperidinyl)methyl]phenyl}carbonyl)amino]methyl}-3-biphenylyl)methyl]-2-methyl-1-piperazinecarboxylate (120 mg, 0.18 mmol) in 5 mL of MeOH, was added 10% Pd/C (60 mg). The mixture was hydrogenated using a hydrogen balloon for 12 hours. After flittering off the catalyst, the mixture was concentrated and the residue was purified by Gilson reverse phase HPLC, eluting with acetonitrile/water/0.1% TFA (10/90 to 70/30, v/v, over 12 min), to give the title compound (65 mg, 41%). LC/MS: m/z, 529 (M+H), 1.29 min.

Example 45

Phenylmethyl (2S)-4-({2'-fluoro-5'-[({[3-(4-piperidinyl)phenyl]carbonyl}amino)methyl]-3-biphenylyl}methyl)-2-methyl-1-piperazinecarboxylate

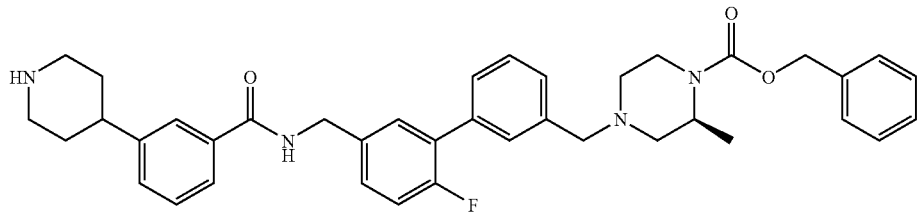

To a solution of the commercially available 3-(1-{[(1,1-dimethylethyl)oxy]carbonyl}-4-piperidinyl)benzoic acid (183 mg, 0.60 mmol) in 2 mL of dry DMF was added phenylmethyl (2S)-4-{[5'-(aminomethyl)-2'-fluoro-3-biphenylyl]methyl}-2-methyl-1-piperazinecarboxylate (250 mg, 0.60 mmol), DIPEA (0.2 ml, 1.4 mmol), and HATU (251 mg, 0.66 mmol). The reaction mixture was stirred at room temperature for 2 h before addition of 2 mL of saturated Na$_2$CO$_3$ and 10 mL of EtOAc. The organic layer was separated, dried over Na$_2$SO$_4$, and filtered. The filtrate was concentrated and the residue was mixed with 4M HCl in 1,4-dioxane (5 mL). The resulting mixture was stirred at room temperature for 1 h. After removal of the solvent, the residue was purified by Gilson reverse phase HPLC, eluting with acetonitrile/water/0.1% TFA (10/90 to 70/30, v/v, over 12 min), to give the title compound (162 mg, 43%). LC/MS: m/z, 635 (M+H), 1.75 min.

Example 46

N-[(3'-{[(3S)-3,4-dimethyl-1-piperazinyl]methyl}-6-fluoro-3-biphenylyl)methyl]-3-(4-piperidinylmethyl)benzamide

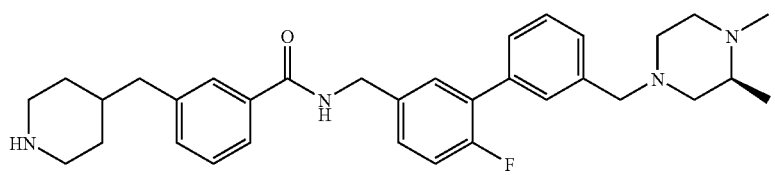

To a solution of 1,1-dimethylethyl 4-{[3-({[(3'-{[(3S)-3,4-dimethyl-1-piperazinyl]methyl}-6-fluoro-3-biphenylyl)methyl]amino}carbonyl)phenyl]methyl)-1-piperidinecarboxylate (250 mg, 0.40 mmol) in 5 mL of 1,4-dioxane was added 4M HCl in 1,4-diozane (5 mL). The mixture was stirred at room temperature for 30 min. After removal of the solvent, the crude was purified by Gilson reverse phase HPLC, eluting with acetonitrile/water/0.1% TFA (10/90 to 70/30, v/v, over 12 min), to give the title compound (200 mg, 95%). LC/MS: m/z, 529 (M+H), 1.27 min.

Example 47

N-[(3'-{[(3S)-3,4-dimethyl-1-piperazinyl]methyl}-6-fluoro-3-biphenylyl)methyl]-3-[(1-methyl-4-piperidinyl)methyl]benzamide

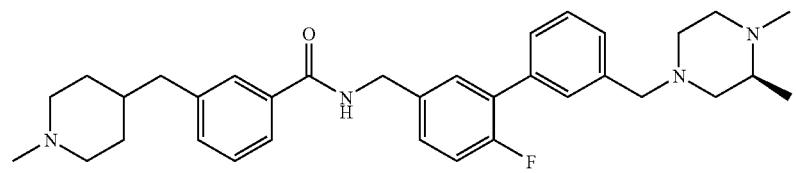

To a solution of N-[(3'-{[(3S)-3,4-dimethyl-1-piperazinyl]methyl}-6-fluoro-3-biphenylyl)methyl]-3-(4-piperidinylmethyl)benzamide (165 mg, 0.313 mmol) in 3 mL of MeOH, was added dropwise formaldehyde (37%, 101 mg, 1.25 mmol). After stirring for 30 minutes, sodium borohydride (24 mg, 0.63 mmol) was added. After stirring of the resulting mixture at rt for 12 hours, the solvent was removed under vacuum and the residue was purified by loading onto a 2 g aminopropyl SPE cartridge and eluting sequentially with DCM (3×5 mL), EtOAc (3×5 mL), and MeOH (3×5 mL). The DCM factions were combined and evaporated to give the title compound as a white solid (60 mg, 35%). LC/MS: m/z, 543 (M+H), 1.18 min.

Example 48

3-(3-amino-4,5-dihydro-1H-pyrazol-1-yl)-N-{[3'-(1-piperazinylmethyl)-3-biphenylyl]methyl}benzamide trifluoroacetate

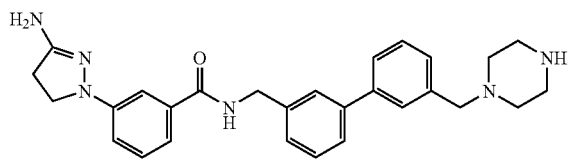

To a solution of (3-(3-amino-4,5-dihydro-1H-pyrazol-1-yl)benzoic acid) (0.1 mmol) in DMF (200 mL) was added a solution of HATU (0.1 mmol) in DMF (100 mL) followed by DIPEA (50 mL). After stirring for 10 minutes at room temperature, the mixture was treated with a solution of {[3'-(1-piperazinylmethyl)-3-biphenylyl]methyl}amine (0.075 mmol) in DMF (200 □l). After stirring for 3 days, the solvent was removed under vacuum. The residue was dissolved in methanol and purified by loading onto a SPE cartridge (SCX, 500 mg), washing with MeOH, and eluting with a 2 M solution of $NH_3$ in MeOH. The solvent was removed under vacuum and the resulting gum was dissolved in 1:1 $CHCl_3$/TFA (0.5 mL). After stirring for 2 hours, the solvent was removed under vacuum to give a crude residue which was further purified by MDAP to afford the title compound as a TFA salt (19.8 mg). LC/MS: m/z, 469 (M+H), 2.21 min.

Example 49

2-[4-(dimethylamino)phenyl]-N-{[3'-(1-piperazinylmethyl)-3-biphenylyl]methyl}acetamide

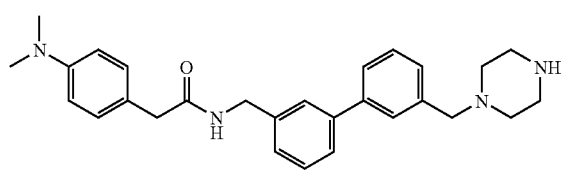

A mixture of PyBOP (0.08 mmol in 200 mL of DMF), {[3'-(1-piperazinylmethyl)-3-biphenylyl]methyl}amine (44 mmol in 200 mL of DMF) and DIPEA (30 mL) were added to [4-(dimethylamino)phenyl]acetic acid (0.07 mmol). The resulting mixture was stirred for 16 hours at room temperature, then the solvent was removed under vacuum. The residue was dissolved in methanol and purified by loading onto a SPE cartridge (SCX, 500 mg), washing with MeOH, and eluting with a 2 M solution of $NH_3$ in MeOH. The $NH_3$ fraction was collected and evaporated under vacuum to give a gum which was dissolved in 1:1 $CHCl_3$/TFA (0.5 mL). After stirring for 2 hours, the solvent was removed under vacuum and the residue was dissolved in MeOH. The free base of the compound was obtained by loading the solution onto a SPE cartridge (SCX, 500 mg), washing with MeOH, and eluting with 2M $NH_3$/MeOH. The ammonia fraction was collected and the solvent was removed under vacuum to give the title compound (14.6 mg). LC/MS: m/z, 443 (M+H), 2.21 min.

Example 50

N-{[3'-(1-piperazinylmethyl)-3-biphenylyl]methyl}-3-(3-pyridinyl)benzamide

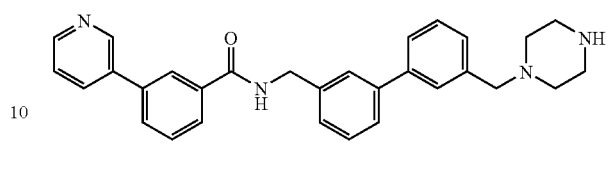

A mixture of PyBOP (0.08 mmol in 200 mL of DMF), {[3'-(1-piperazinylmethyl)-3-biphenylyl]methyl}amine (440 □mol in 200 mL of DMF) and DIPEA (30 mL) were added to 3-(3-pyridinyl)benzoic acid (0.07 mmol). The resulting mixture was stirred for 16 hours at room temperature, then the solvent was removed under vacuum. The residue was redissolved in methanol and purified by loading onto a SPE cartridge (SCX, 500 mg), washing with MeOH, and eluting with a 2 M solution of $NH_3$ in MeOH. The $NH_3$ fraction was collected and evaporated under vacuum to give a gum which was redissolved in 1:1 $CHCl_3$/TFA (0.5 mL). After stirring for 2 hours, the solvent was removed under vacuum and the residue was purified by MDAP to give the desired compound as a TFA salt. The free base of the compound was obtained by loading the salt onto a SPE cartridge (SCX, 500 mg), washing with MeOH, and eluting with 2 M $NH_3$/MeOH. The ammonia fraction was collected and the solvent was removed under vacuum to give the title compound (14 mg). LC/MS: m/z, 463 (M+H), 2.32 min.

The compounds listed in Table 3 were prepared proceeding in a similar manner to Example 50 but replacing 3-(3-pyridinyl)benzoic acid with the appropriate acid.

TABLE 3

| Example | R | MS [M+] | Rt |
|---|---|---|---|
| 51 | (piperidin-1-yl)ethyl | 421 | 1.92 |
| 52 | phenylamino-ethyl | 415 | 2.36 |
| 53 | 4-(dimethylamino)phenyl | 429 | 2.42 |

TABLE 3-continued

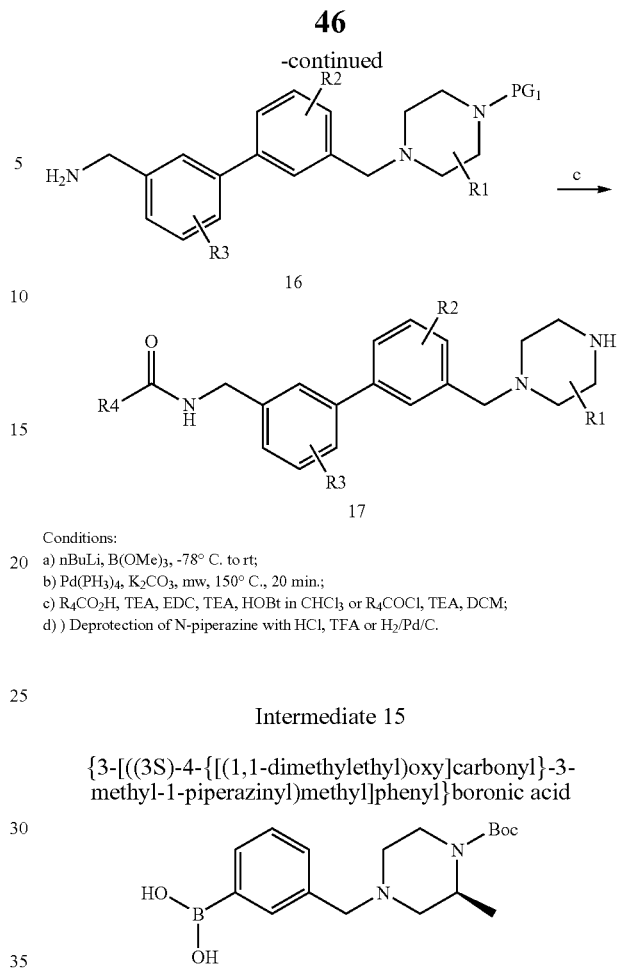

| Example | R | MS [M+] | Rt |
|---|---|---|---|
| 54 | (2-dimethylamino-phenyl, t-Bu) | 429 | 2.25 |
| 55 | (4-methylamino-phenyl, t-Bu) | 415 | 2.32 |
| 56 | (2-t-Bu-4-(pyridin-3-yl)thiazole) | 470 | 2.37 |

Preparation 4

Scheme 4 outlines an alternative solution phase route to compounds of structure 17. Boronation of 14 using trimethyl borate led to the boronic acids 18. Further Suzuki coupling of 18 with the benzyl bromide derivatives 19 produced compounds 16, which in turn could be coupled with the appropriate carboxylic acids R₄CO₂H or acyl halides and deprotected to furnish the products 17.

Scheme 4

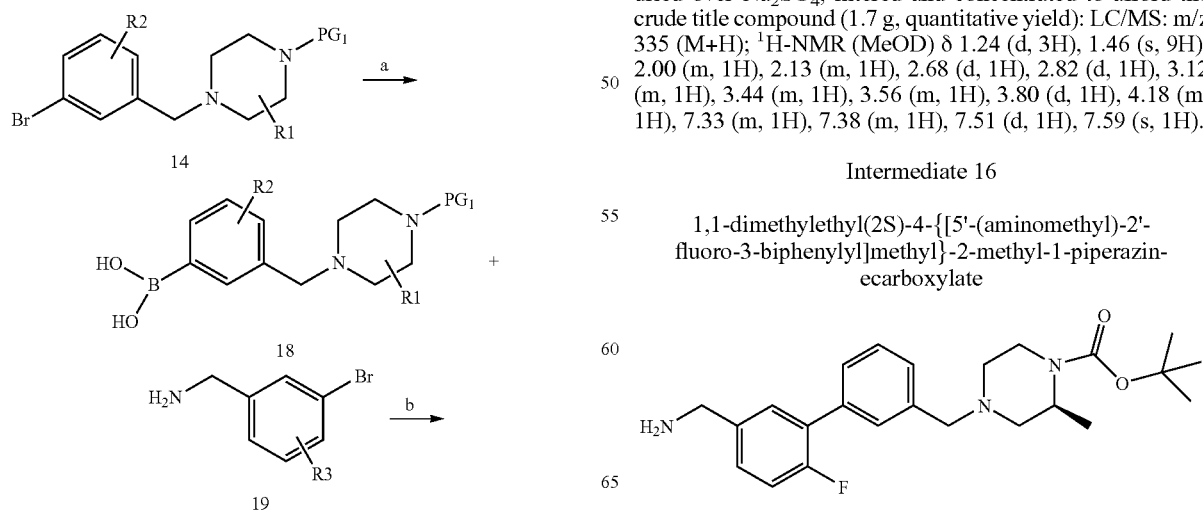

Conditions:
a) nBuLi, B(OMe)₃, −78° C. to rt;
b) Pd(PH₃)₄, K₂CO₃, mw, 150° C., 20 min.;
c) R₄CO₂H, TEA, EDC, TEA, HOBt in CHCl₃ or R₄COCl, TEA, DCM;
d) ) Deprotection of N-piperazine with HCl, TFA or H₂/Pd/C.

Intermediate 15

{3-[((3S)-4-{[(1,1-dimethylethyl)oxy]carbonyl}-3-methyl-1-piperazinyl)methyl]phenyl}boronic acid A solution of 1,1-dimethylethyl (2S)-4-[(3-bromophenyl)methyl]-2-methyl-1-piperazine carboxylate (1.8 g, 4.9 mmol) in THF (4.9 mL) was mixed with nBuLi (3.7 mL, 1.6 M in Hexane, 5.9 mmol) at −78° C. and stirred for 30 min before B(OMe)₃ (2.2 mL, 19.6 mmol) was added. After addition, the resulting solution was warmed up to room temperature within 2 hours. The mixture was then mixed with saturated aqueous NH₄Cl solution (10 mL), stirred for 25 minutes at room temperature, diluted with H₂O (5 mL) and extracted with Et₂O (2×30 mL). The organic layers were collected, dried over Na₂SO₄, filtered and concentrated to afford the crude title compound (1.7 g, quantitative yield): LC/MS: m/z 335 (M+H); ¹H-NMR (MeOD) δ 1.24 (d, 3H), 1.46 (s, 9H), 2.00 (m, 1H), 2.13 (m, 1H), 2.68 (d, 1H), 2.82 (d, 1H), 3.12 (m, 1H), 3.44 (m, 1H), 3.56 (m, 1H), 3.80 (d, 1H), 4.18 (m, 1H), 7.33 (m, 1H), 7.38 (m, 1H), 7.51 (d, 1H), 7.59 (s, 1H).

Intermediate 16

1,1-dimethylethyl(2S)-4-{[5'-(aminomethyl)-2'-fluoro-3-biphenylyl]methyl}-2-methyl-1-piperazinecarboxylate To a solution of [(3-bromo-4-fluorophenyl)methyl]amine hydrochloride (1.68 g, 7 mmol) in dioxane/H$_2$O (10 mL/3.3 mL) was added {3-[((3S)-4-{[(1,1-dimethylethyl)oxy]carbonyl}-3-methyl-1-piperazinyl)methyl]phenyl}boronic acid (2.33 g, 7 mmol), K$_2$CO$_3$ (4.83, 35 mmol) and Pd(PPh$_3$)$_4$ (405 mg, 0.35 mmol). The resulting mixture was heated at 150° C. in a pressure vessel for 2 hours, then cooled to rt and diluted with EtOAc (50 mL). The organic layer was collected and the aqueous layer was extracted by EtOAc (30 mL). The organic layers were combined, dried over Na$_2$SO$_4$, filtered and concentrated. The residue was purified by Gilson preparatory HPLC, eluting with acetonitrile/water/0.1% TFA (10/90 to 90/10, v/v, over 12 min), to give the title compound (1.08 g, 37%). LC/MS: m/z, 414 (M+H), 1.83 min.

Example 57

N-[(6-fluoro-3'-{[(3S)-3-methyl-1-piperazinyl]methyl}-3-biphenylyl)methyl]-3-(4-piperidinylmethyl) benzamide

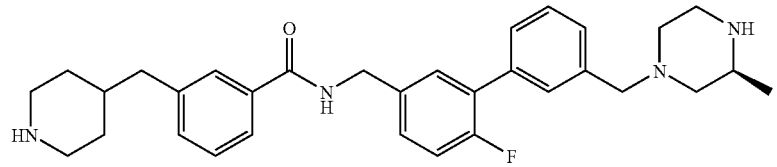

To a solution of 1,1-dimethylethyl(2S)-4-{[5'-(aminomethyl)-2'-fluoro-3-biphenylyl]methyl}-2-methyl-1-piperazinecarboxylate (25 mg, 0.06 mmol) in CHCl$_3$ (5 mL) was added 3-[(1-{[(1,1-dimethylethyl)oxy]carbonyl}-4-piperidinyl)methyl]benzoic acid (28.7 mg, 0.09 mmol), EDC (12 mg, 0.06 mmol), HOBT (1 mg, 0.006 mmol) and diisopropyl ethylamine (0.1 mL). The resulting mixture was stirred for 12 hours at rt, concentrated under vacuum and purified by combiflash to provide the desired BOC protected amide. The residue was dissolved in CH$_2$Cl$_2$ (2 mL) and the resulting solution was mixed with TFA (0.7 mL) at 0° C. After stirring at ambient temperature for 12 hours, Et$_3$N (0.1 mL) was added to the reaction mixture at −78° C. After removal of the solvent under vacuum, the residue was purified by Gilson reverse phase HPLC, eluting with acetonitrile/water/0.1% TFA (10/90 to 70/30, v/v, over 12 min), to give the title compound (20 mg, 93%). LC/MS (ES) m/z 515 (M+H)$^+$; $^1$HNMR (MeOD) δ1.3 (1H, m), 1.4 (3H, d), 1.5 (2H, m), 2.0 (5H, m), 2.7 (2H, d), 2.9 (3H, m), 3.2 (1H, m), 3.6 (4H, s), 4.3 (2H, s), 4.6 (2H, s), 7.3 (1H, t), 7.4 (3H, m), 7.55 (3H, m), 7.65 (1H, m), 7.7 (1H, m).

Example 58

N-[(6-fluoro-3'-{[(3S)-3-methyl-1-piperazinyl]methyl}-3-biphenylyl)methyl]-3-(4-piperidinyl)benzamide

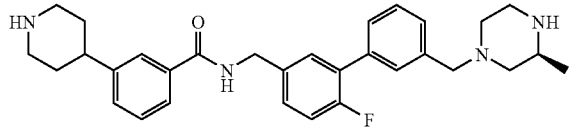

Following the standard procedure outlined in Example 57, 1,1-dimethylethyl (2S)-4-{[5'-(aminomethyl)-2'-fluoro-3-biphenylyl]methyl}-2-methyl-1-piperazinecarboxylate, 50 mg, 0.121 mmol) was reacted with the commercially available 3-(1-{[(1,1-dimethylethyl)oxy]carbonyl}-4-piperidinyl)benzoic acid (37 mg, 0.121 mmol) to give the title compound (11 mg, 18%). LC/MS: m/z, 501 (M+H), 1.27 min.

Example 59

N-(6-fluoro-3'-{[(3S)-3-methyl-1-piperazinyl]methyl}-3-biphenylyl)methyl]-4-(4-piperidinylmethyl) benzamide

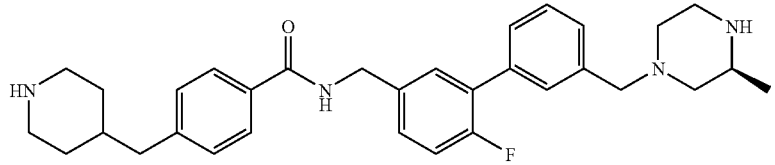

Following the standard procedure outlined in Example 57, 1,1-dimethylethyl (2S)-4-{[5'-(aminomethyl)-2'-fluoro-3-biphenylyl]methyl}-2-methyl-1-piperazinecarboxylate (50 mg, 0.121 mmol) was reacted with the commercially available 4-[(1-{[(1,1-dimethylethyl)oxy]carbonyl}-4-piperidinyl)methyl]benzoic acid (39 mg, 0.121 mmol) to give the title compound 63 mg (61%). LC/MS: m/z, 515 (M+H), 1.41 min.

Preparation 5

Alternatively, compounds of structure 17 can be prepared using solid phase chemistry as depicted in Scheme 5. 3-Bromo substituted benzylamines 20 were loaded onto DMHB resin. The resin-bound amines 21 were then coupled with carboxylic acids to yield the amides 22, which underwent Suzuki coupling to give the biphenylaldehydes 23. Further reductive alkylation of 23 with (2S)-2-methylpiperazine, followed by cleavage of the resin, afforded the products 17.

Scheme 5

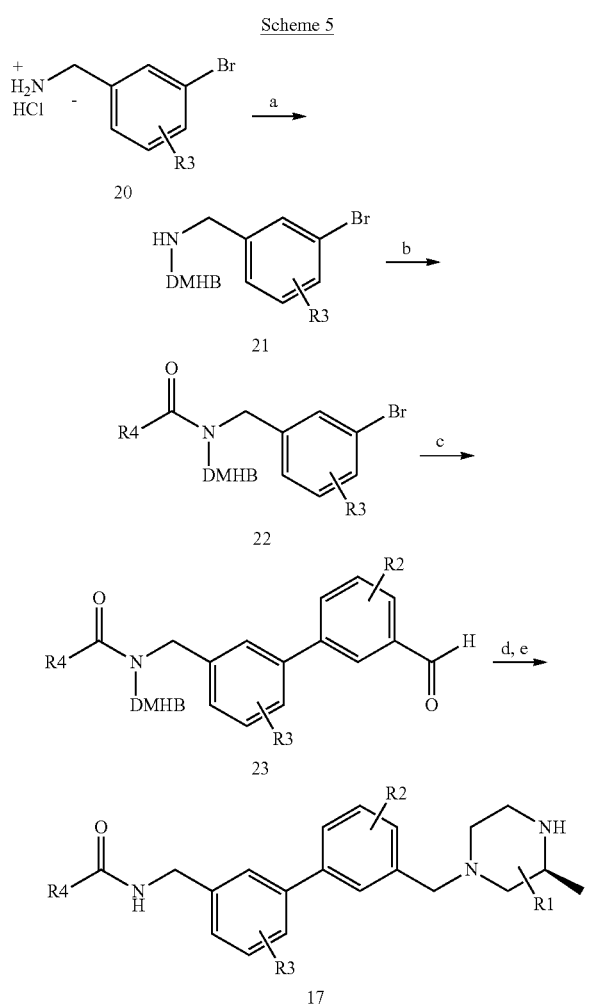

Conditions:
a) DMHB resin, Na(OAc)₃BH, DIEA, HOAc, NMP, rt;
b) R₄CO₂H, DIC, DCM/DMF = 1:1, rt;
c) formyl substituted phenyl- boronic acid, 5% Pd(PPh₃)₄, Na₂CO₃, DME, 80° C.;
d) (2S)-2-methylpiperazine, Na(OAc)₃BH, Na₂SO₄, DCM, rt;
e) 20% TFA in DCM, rt.

Example 60

3-(dimethylamino)-N-[(3'-{[(3S)-3-methyl-1-piperazinyl]methyl}-3-biphenylyl)methyl]benzamide

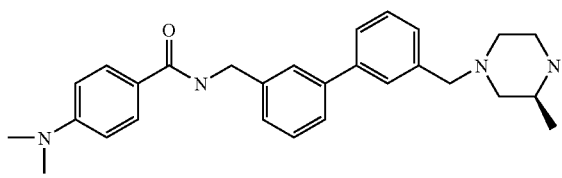

Into a 250 mL glass shaker, was added 2,6-dimethoxy-4-polystyrenebenzyloxy-benzaldehyde (DMHB resin) (10 g, 1.5 mmol/g, 15 mmol) and 150 mL NMP. 3-Bromo-benzylamine HCl salt (17 g, 75 mmol) was then added, followed by DIPEA (13 mL, 75 mmol), HOAc (15 mL, 10%) and Na(OAc)₃BH (19.1 g, 90 mmol). The mixture was shaken at RT for 12 hours. The resin-bound 3-bromo-benzylamine was then washed with NMP (2×150 mL), DCM (2×150 mL), MeOH (2×150 mL) and DCM (2×150 mL), dried in a vacuum oven at 35° C. for 12. The loading was estimated at 100%.

To the above resin-bound 3-bromo-benzylamine (0.5 g, 1.2 mmol/g, 0.6 mmol) in DCE/DMF (1:1, 20 mL) was added p-(N,N-dimethyl)aminobenzoic acid (1.0 g, 6 mmol), followed by DIC (0.925 mL, 6 mmol). The resulting mixture was shaken at rt for 12 hours. The resin was then washed with DMF (2×25 mL), DCM (2×25 mL), MeOH (2×25 mL) and DCM (2×25 mL), and dried in vacuum oven at 35° C. for 12 hours. An analytical amount of the resin was cleaved with 20% of TFA in DCM for 10 min. The resulting solution was concentrated under vacuum and redissolved in 0.5 mL of MeOH for LC/MS. MS (ESI): 333 [M+H]⁺.

To the above resin-bound N-[(3-bromophenyl)methyl]-N,N-dimethyl-aminobenzamide (0.6 g, 1.0 mmol/g, 0.6 mmol) in DME (15 mL) was added 3-formylphenyl-boronic acid (0.27 g, 1.8 mmol). After addition of a 2 M K₂CO₃ aqueous solution (0.9 mL, 1.8 mmol) and Pd(PPh₃)₄ (0.036 g, 0.03 mmol), the reaction mixture was purged with argon for 10 min. The reactor was heated at 80° C. for 10 h. The resin was washed with THF (2×20 mL), THF:H₂O (1:1, 2×20 mL), H₂O (2×20 mL), THF:H₂O (1:1, 2×20 mL), THF (2×20 mL), DCM (2×20 mL), and dried in vacuum oven at 35° C. for overnight. An analytical amount of the resin was cleaved with 20% of TFA in DCM for 10 min. The resulting solution was concentrated under vacuum and redissolved in 0.5 mL of CH₃CN for LC-MS. MS (ESI): 413 [M+H]⁺.

To the above resin-bound N-[(3-formylphenyl)methyl]-N,N-dimethyl-aminobenzamide (100 mg, 0.84 mmol/g, 0.084 mmol) in DCE was added Na₂SO₄ (0.06 g, 0.42 mmol), followed by (2S)-2-methylpiperazine (0.042 g, 0.42 mmol). After shaking for a 10 min, Na(OAc)₃BH (0.11 g, 0.5 mmol) was added to the reaction vessel. The resulting mixture was shaken at rt for a further 12 hours. The resin was then washed with THF (2×25 mL), THF:H₂O (1:1, 2×25 mL), H₂O (2×25 mL), THF:H₂O (1:1, 2×25 mL), THF (2×25 mL), DCM (2×25 mL), and dried in a vacuum oven at 35° C. for 12 hours. The resin was then cleaved off with 20% of TFA in DCM for 30 min (×2). The resulting solution was concentrated under vacuum. The residue was dissolved in DMSO (0.6 mL) and purified using a Gilson semi-preparative HPLC system to give 20 mg of the title compound. LC/MS (ES) m/z 443 (M+H)⁺; r.t. 1.48 min; ¹HNMR (MeOD) δ 1.38 (3H, d), 3.05 (1H, m), 3.08 (6H, s), 3.20 (1H, t), 3.45 (1H, t), 3.66 (4H, m), 4.38 (2H, s), 4.65 (2H, s), 6.90 (2H, d), 7.49 (3H, m), 7.56 (2H, m), 7.66 (1H, s), 7.74 (1H, d), 7.83 (2H, m).

Example 61

N-[(3'-{[(3S)-3-methyl-1-piperazinyl]methyl}-3-biphenylyl)methyl]-3-(4-piperidinylmethyl)benzamide

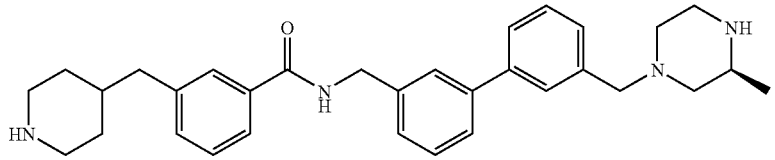

Following the standard procedure outlined in Example 60, using 3-(4-piperidinylmethyl)benzoic acid as the carboxylic acid, 46 mg of the title compound were obtained. LC/MS: m/z 498 (M+H), ¹HNMR (MeOD) δ 1.40 (5H, m), 1.90 (3H, m), 2.70 (2H, t), 2.91 (2H, t), 3.16 (1H, t), 3.25 (1H, m), 3.39 (2H, m), 3.46 (1H, t), 3.66 (4H, m), 4.41 (2H, s), 4.67 (2H, s), 7.40 (4H, m), 7.49 (1H, m), 7.57 (2H, m), 7.60 (1H, s), 7.73 (3H, m), 7.83 (1H, s).

Preparation 6

The aromatic derivatives of general structure 28 could also be prepared as depicted in Scheme 6. Reductive amination of carboxaldehyde derivatives 24 with the protected piperazines 12 gave the tertiary amines 25. Further palladium coupling of 25 with aminomethyl boronic acids 26 produced compounds 27, which in turn could be coupled to the appropriate carboxylic acids R₄CO₂H to furnish the products 28.

Scheme 6

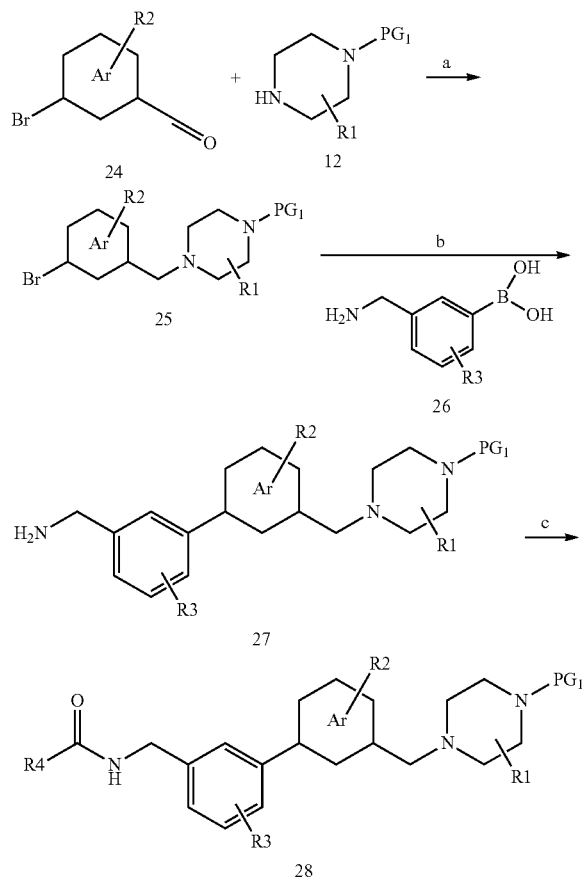

Conditions:
a) NaB(OAc)₃H, DCM, rt;
b) Pd(PH₃)₄, K₂CO₃, mw, 150° C., 20 min.;
c) R₄CO₂H, TEA, EDC, HOBt in CHCl₃ then TFA.

Intermediate 17

1,1-Dimethylethyl (2S)-4-[(5-bromo-2-thienyl)methyl]-2-methyl-1-piperazinecarboxylate

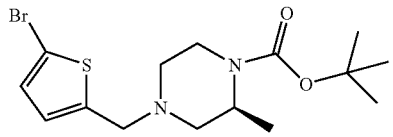

Following the standard procedure outlined for intermediate 2,1,1-dimethylethyl (2S)-2-methyl-1-piperazinecarboxylate (1.0 g, 5 mmol) was reacted with 5-bromo-2-thiophenecarbaldehyde (0.96 g, 5 mmol) to give the title compound (1.43 g, 76%). LCMS: m/z, 375 (M+H), 1.63 min.

Intermediate 18

1,1-dimethylethyl (2S)-4-({5-[3-(aminomethyl)phenyl]-2-thienyl}methyl)-2-methyl-1-piperazinecarboxylate

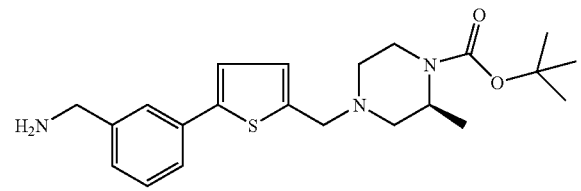

To the solution of [3-(aminomethyl)phenyl]boronic acid hydrochloride (325 mg, 1.2 mmol) in dioxane/H₂O (10 mL/3.3 mL) was added 1,1-dimethylethyl (2S)-4-[(5-bromo-2-thienyl)methyl]-2-methyl-1-piperazinecarboxylate (450 mg, 1.2 mmol), K₂CO₃ (828 mg, 6.0 mmol) and Pd(PPh₃)₄ (70 mg, 0.06 mmol). The resulting solution was irradiated in a microwave reactor at 150° C. for 20 minutes and diluted with EtOAc (5 mL). The organic layer was collected and the aqueous layer was extracted by EtOAc (2×5 mL). The organic layers were combined, dried over Na₂SO₄, filtered and concentrated. The residue was purified by Gilson HPLC, eluting with acetonitrile/water/0.1% TFA (10/90 to 90/10, v/v, over 12 min), to give the title compound (200 mg, 42%). LC/MS: m/z, 402 (M+H), 1.24 min.

Example 62

N-{[3-(5-{[(3S)-3-methyl-1-piperazinyl]methyl}-2-thienyl)phenyl]methyl}-3-(4-piperidinylmethyl)benzamide

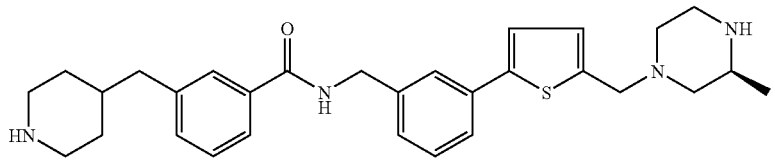

To a solution of 3-[(1-{[(1,1-dimethylethyl)oxy]carbonyl}-4-piperidinyl)methyl]benzoic acid (319 mg, 1.0 mmol) in CHCl₃ (5.0 mL) was added 1,1-dimethylethyl (2S)-4-({5-[3-(aminomethyl)phenyl]-2-thienyl}methyl)-2-methyl-1-piperazinecarboxylate (401 mg, 1.0 mmol), TEA (0.26 ml, 2 mmol), EDC (288 mg, 1.5 mmol) and HOBt (150 mg, 1.1 mmol). The reaction mixture was stirred at room temperature for 2 h, followed by addition of 1 mL of saturated Na₂CO₃. The organic layer was dried over Na₂SO₄, and filtered. The filtrate was mixed with 1 mL of TFA, and stirred at room temperature for 1 h. After removal of the solvent, the residue was purified by Gilson reverse phase HPLC, eluting with acetonitrile/water/0.1% TFA (10/90 to 70/30, v/v, over 12 min), to give the title compound (261 mg, 52%). LC/MS: m/z, 502 (M+H), 1.31 min.

Intermediate 19

1,1-dimethylethyl (2S)-4-[(6-bromo-2-pyridinyl)methyl]-2-methyl-1-piperazinecarboxylate

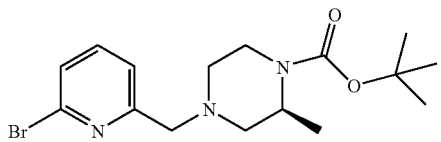

Following the standard procedure outlined for intermediate 2, 1,1-dimethylethyl (2S)-2-methyl-1-piperazinecarboxylate (1.0 g, 5 mmol) was reacted with 6-bromo-2-pyridine carboxaldehyde (1.0 g, 5.4 mmol) to give the title compound 1.6 g (80%). LC/MS: m/z, 370 (M), 1.43 min.

Intermediate 20

1,1-dimethylethyl (2S)-4-([{6-[3-(aminomethyl)phenyl]-2-pyridinyl}methyl)-2-methyl-1-piperazinecarboxylate

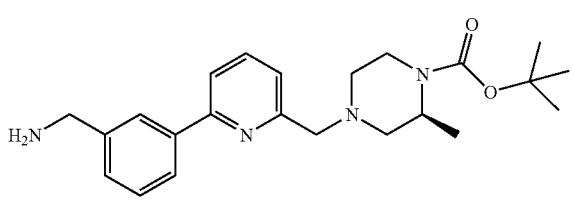

Following the standard procedure outlined for Intermediate 18, 1,1-dimethylethyl (2S)-4-[(6-bromo-2-pyridinyl)methyl]-2-methyl-1-piperazinecarboxylate (430 mg, 1.16 mmol) was reacted with [3-(aminomethyl)phenyl]boronic acid (314 mg, 1.16 mmol) to give the title compound 420 mg (92%). LC/MS: m/z, 397 (M+H), 1.22 min.

Example 63

N-{[3-(6-{[(3S)-3-methyl-1-piperazinyl]methyl}-2-Pyridinyl)Phenyl]methyl}-3-(4-piperidinylmethyl)benzamide

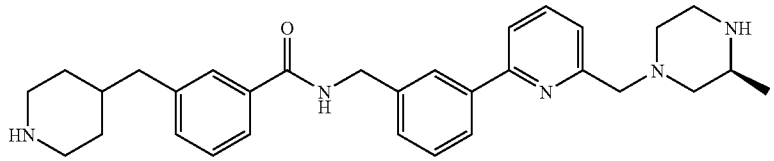

To a solution of the commercially available 3-[(1-{[(1,1-dimethylethyl)oxy]carbonyl}-4-piperidinyl)methyl]benzoic acid (40 mg, 0.13 mmol) in CHCl₃ (2.0 mL) was added 1,1-dimethylethyl (2S)-4-({6-[3-(aminomethyl)phenyl]-2-pyridinyl}methyl)-2-methyl-1-piperazinecarboxylate (50 mg, 0.13 mmol), TEA (0.04 ml, 0.3 mmol), EDC (36 mg, 0.19 mmol) and HOBt (18 mg, 0.14 mmol). The reaction mixture was stirred at room temperature for 2 h, followed by addition of 0.5 mL of saturated Na₂CO₃. The organic layer was isolated via a hydrophobic frit followed by addition of 0.5 mL of TFA, and stirred at room temperature for 1 h. After removal of the solvent, the residue was purified by Gilson reverse phase HPLC, eluting with acetonitrile/water/0.1% TFA (10/90 to 70/30, v/v, over 12 in), to give the title compound (23 mg, 19%). LC/MS: m/z, 499 (M+H), 1.19 min.

Example 64

N-{[3-(6-[([(3S)-3-methyl-1-piperazinyl]methyl}-2-Pyridinyl)phenyl]methyl}-3-(4-piperidinyl)benzamide

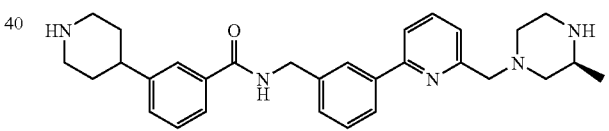

Following the standard procedure outlined in Example 63, 1,1-dimethylethyl (2S)-4-({6-[3-(aminomethyl)phenyl]-2-pyridinyl}methyl)-2-methyl-1-piperazinecarboxylate (50 mg, 126 mmol) was reacted with the commercially available 3-(4-piperidinyl)benzoic acid (38 g, 126 mmol) to give the title compound (43 mg, 36%). LC/MS: m/z, 484 (M+), 1.17 min.

Intermediate 21

1,1-dimethylethyl (2S)-4-({3-[5-(aminomethyl)-2-thienyl]phenyl}methyl)-2-methyl-1-piperazinecarboxylate

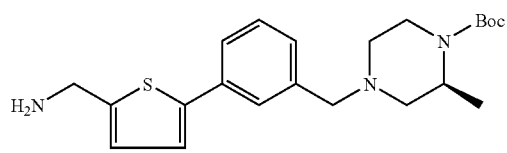

Following the standard procedure outlined for Intermediate 18, 1,1-dimethylethyl (2S)-4-[(3-bromophenyl)methyl]-2-methyl-1-piperazine carboxylate (333 mg, 1 mmol) was reacted with the commercially available [(3-(aminomethyl)phenyl]boronic acid hydrochloride (325 mg, 1.2 mmol) to give the title compound (200 mg, 40%). LC/MS: m/z, 402 (M+H), 1.24 min.

Example 65

N-{[5-(3-{[(3S)-3-methyl-1-piperazinyl]methyl}phenyl)-2-thienyl]methyl}-3-(4-piperidinylmethyl)benzamide

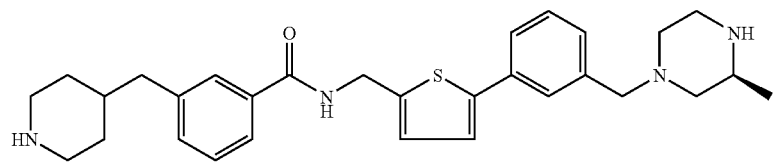

To a solution of 3-[(1-{[(1,1-dimethylethyl)oxy]carbonyl}-4-piperidinyl)methyl]benzoic acid (128 mg, 0.40 mmol) in CHCl₃ (2.0 mL) was added 1,1-dimethylethyl (2S)-4-({3-[5-(aminomethyl)-2-thienyl]phenyl}methyl)-2-methyl-1-piperazinecarboxylate (160 mg, 0.40 mmol), TEA (0.1 ml, 0.7 mmol), EDC (115 mg, 0.6 mmol) and HOBt (59 mg, 0.44 mmol). The reaction mixture was stirred at room temperature for 2 h, followed by addition of 0.5 mL of saturated Na₂CO₃. The organic layer was isolated via a hydrophobic frit followed by addition of 0.5 mL of TFA, and stirred at room temperature for 1 h. After removal of the solvent, the residue was purified by Gilson reverse phase HPLC, eluting with acetonitrile/water/0.1% TFA (10/90 to 70/30, v/v, over 12 min), to give the title compound (100 mg, 50%). LC/MS: m/z, 503 (M+H), 1.22 min.

Preparation 7

The substituted amide derivatives of general structure 32 were prepared in solution phase as depicted in Scheme 7. Peptide coupling between benzoic acids 29 and primary amine derivatives 20 led to amides 30, which in turn underwent a Suzuki palladium coupling to boronic acids 18, to give compounds 31. Subsequent N-alkylation of 31 with appropriate alkylating agents gave, after deprotection, the corresponding products 32.

Scheme 7

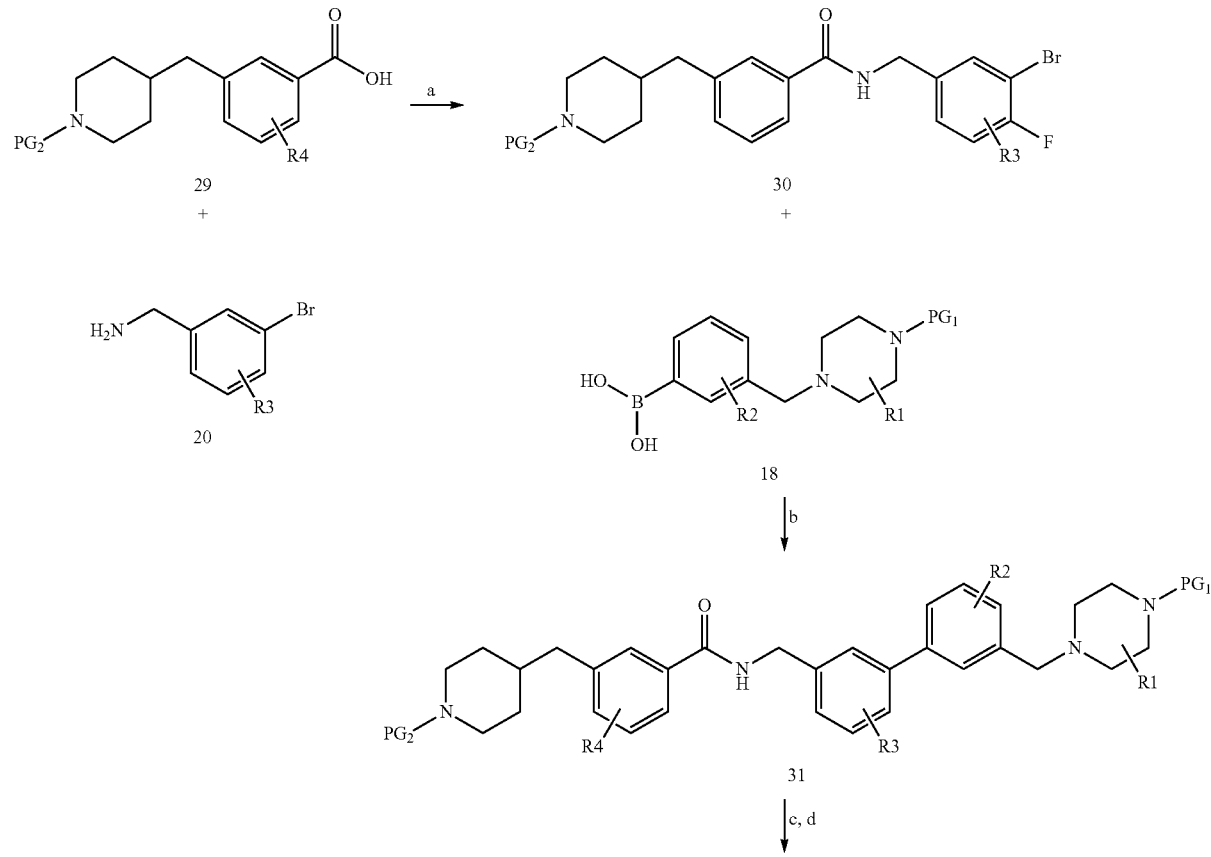

-continued

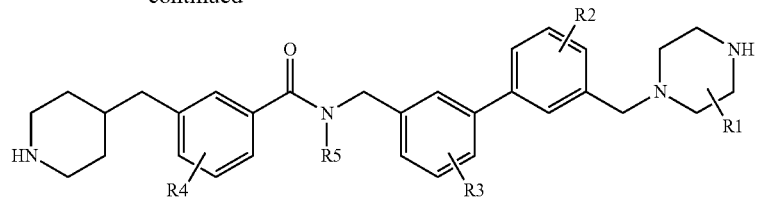

Conditions:
a) HATU, DIPEA, DMF;
b) Pd(PPh3)4, Na2CO3, DME, 78° C.;
c) NaH, R4Br, DMF;
d) Removal of the protecting groups Example 66

Preparation of N-[(6-fluoro-3'-{[(3S)-3-methyl-1-piperazinyl]methyl}-3-biphenylyl)methyl]-N-methyl-3-(4-piperidinylmethyl)benzamide 1,1-Dimethylethyl 4-{[3-({[(3-bromo-4-fluorophenyl)methyl]amino}carbonyl)phenyl]methyl}-1-piperidinecarboxylate To a solution of [(3-bromo-4-fluorophenyl)methyl]amine (0.802 g, 3.33 mmol) in DMF (12.0 mL) was added 3-[(1-{[(1,1-dimethylethyl)oxy]carbonyl}-4-piperidinyl)methyl] benzoic acid (1.060 g, 3.32 mmol), HATU (1.389 g, 3.65 mmol), and diisopropylethylamine (2.9 mL, 16.6 mmol). The reaction was allowed to stir at room temperature overnight. The reaction was diluted with EtOAc (300 mL), washed with 1N HCl (2×75 mL), then saturated NaHCO$_3$ (3×75 mL), then brine (2×75 mL). The organic layer was dried over MgSO$_4$, filtered, and concentrated under vacuum to give the desired product (1.58 g, 94.2%). EI-MS m/z 506(M−H)$^+$.

1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate To a solution of {3-[((3S)-4-{[(1,1-dimethylethyl)oxy]carbonyl}-3-methyl-1-piperazinyl)methyl]phenyl}boronic acid (0.7278 g, 2.18 mmol) in DME (20 mL) was added 1,1-dimethylethyl 4-{[3-({[(3-bromo-4-fluorophenyl)methyl]amino}carbonyl)phenyl]methyl}-1-piperidinecarboxylate (1.091 g, 2.15 mmol) followed by Na$_2$CO$_3$ (6.5 mL, 2M in H$_2$O, 13.0 mmol). The reaction vessel was flushed with Ar, and tetrakis(triphenylphosphine)palladium(0) (0.2427 g, 0.210 mmol) was added. The reaction mixture was heated at 78° C. under Ar for 12 hours. The reaction was diluted with EtOAc (300 mL) and washed with H$_2$O (250 mL). The water layer was extracted with EtOAc (1×50 mL). The combined organic layers were dried over MgSO$_4$, filtered, and concentrated under vacuum. Purification of the crude residue by flash chromatography (20% EtOAc/80% DCM) on silica gel gave the title compound (0.707 g, 45.8%). EI-MS m/z 716 (M−H)$^+$.

General Procedure for Secondary Amide Formation

N-[(6-Fluoro-3'-{[(3S)-3-methyl-1-piperazinyl]methyl}-3-biphenylyl)methyl]-N-methyl-3-(4-piperidinylmethyl)benzamide To a solution of 1,1-dimethylethyl (2S)-4-[(5'-{[({3-[(1-{[(1,1-dimethylethyl)oxy]carbonyl}-4-piperidinyl)methyl] phenyl}carbonyl)amino]methyl}-2'-fluoro-3-biphenylyl)methyl]-2-methyl-1-piperazinecarboxylate (47.3 mg, 0.0662 mmol) in DMF (2.5 mL) at 0° C. was added NaH (95%, 6.62 mg, 0.262 mmol). The reaction was stirred for 15 minutes, and then a solution of MeBr (2 M in Et$_2$O, 0.10 mL, 0.20 mmol) in DMF (0.5 mL) was added. The reaction was allowed to warm up to room temperature for 12 hours [when the reaction was not complete, as assessed by LC/MS, after 12 hours, 2 equivalents of NaH and of the bromide derivative were added and the reaction was allowed to stir for another 12 hours]. The reaction mixture was then diluted with MeOH (2.5 mL), HCl (4N in 1,2-dioxane, 2.5 mL) was added and the resulting mixture was allowed to stir at room temperature for 12 hours. The reaction mixture was then concentrated under vacuum, and the residue was taken up in DMSO/MeOH (1:1) and purified via MDAP (10-90% CH$_3$CN/H$_2$O/(0.1% TFA)). The desired fractions were isolated, and then taken up in DCM (8 mL) and 1N NaOH (8 mL) and allowed to stir for 2 hours. The DCM layer was isolated using a phase separator and then concentrated under vacuum to give the title compound (37.0 mg, 100%). EI-MS m/z 529(M−H)$^+$.

Example 67

Preparation of N-ethyl-N-[(6-fluoro-3'-{[(3S)-3-methyl-1-piperazinyl]methyl}-3-biphenylyl)methyl]-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl] phenyl}carbonyl)amino]methyl}-2'-fluoro-3-biphenylyl)methyl]-2-methyl-1-piperazinecarboxylate (75.4 mg, 0.105 mmol), NaH (5.37 mg, 0.243 mmol) and bromoethane (0.0095 mL, 0.127 mmol) in DMF (0.5 mL) were reacted to give the desired product (19.2 mg, 33.6%). EI-MS m/z 543 (M−H)$^+$.

Example 68

Preparation of N-(6-fluoro-3'-{[(3S)-3-methyl-1-piperazinyl]methyl}-3-biphenylyl)methyl]-N-[3-(methyloxy)propyl]-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl] phenyl}carbonyl)amino]methyl}-2'-fluoro-3-biphenylyl)methyl]-2-methyl-1-piperazinecarboxylate (75.4 mg, 0.105 mmol), NaH (5.37 mg, 0.243 mmol) and 3-bromopropyl methyl ether (25.2 mg 0.165 mmol) in DMF (0.5 mL) were reacted to give the desired product (23.2 mg, 37.4%). EI-MS m/z 587(M−H)+.

Example 69

Preparation of N-[(6-fluoro-3'-{[(3S)-3-methyl-1-piperazinyl]methyl}-3-biphenylyl)methyl]-N-[3-(phenyloxy)propyl]-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl)-2'-fluoro-3-biphenylyl)methyl]-2-methyl-1-piperazinecarboxylate (75.4 mg, 0.105 mmol), NaH (5.37 mg, 0.243 mmol) and 3-bromopropyl phenyl ether (0.020 mL, 0.127 mmol) in DMF (0.5 mL) were reacted to give the desired product (16.4 mg, 24.0%). EI-MS m/z 649(M−H)+.

Example 70

Preparation of N-[(6-fluoro-3'-{[(3S)-3-methyl-1-piperazinyl]methyl}-3-biphenylyl)methyl]-N-hexyl-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (75.4 mg, 0.105 mmol), NaH (5.37 mg, 0.243 mmol) and 1-bromohexane (0.020 mL, 0.142 mmol) in DMF (0.5 mL) were reacted to give the desired product (16.4 mg, 24.0%). EI-MS m/z 599 (M−H)+.

Example 71

Preparation of N-(cyclohexylmethyl)-N-[(6-fluoro-3'-{[(3S)-3-methyl-1-piperazinyl]methyl}-3-biphenylyl)methyl]-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (47.3 mg, 0.0662 mmol), NaH (6.62 mg, 0.262 mmol) and (bromomethyl)cyclohexane (0.0150 mL, 0.108 mmol) in DMF (1.0 mL) were reacted to give the desired product (7.9 mg, 19.6%). EI-MS m/z 611 (M−H)+.

Example 72

Preparation of N-[(6-fluoro-3'-{[(3S-3-methyl-1-piperazinyl]methyl}-3-biphenylyl)methyl]-N-nonyl-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (47.3 mg, 0.0662 mmol), NaH (6.62 mg, 0.262 mmol) and 1-bromononane (24.9 mg, 0.120 mmol) in DMF (1.0 mL) were reacted to give the desired product (12.3 mg, 29.0%). EI-MS m/z 641 (M−H)+.

Example 73

Preparation of N-[(6-fluoro-3'-{[(3S)-3-methyl-1-piperazinyl]methyl-3-biphenylyl)methyl]-N(Phenylmethyl)-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (47.3 mg, 0.0662 mmol), NaH (6.62 mg, 0.262 mmol) and (bromomethyl)benzene (0.0130 mL, 0.109 mmol) in DMF (1.0 mL) were reacted to give the desired product (16.7 mg, 41.8%). EI-MS m/z 605(M−H)+.

Example 74

Preparation of N-(cyclopropylmethyl)-N-[(6-fluoro-3'-{[(3S)-3-methyl-1-piperazinyl]methyl}-3-biphenylyl)methyl]-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (76.1 mg, 0.106 mmol), NaH (8.29 mg, 0.345 mmol) and (bromomethyl)cyclopropane (0.0155 mL, 0.160 mmol) in DMF (1.0 mL) were reacted to give the desired product (8.4 mg, 13.7%). EI-MS m/z 569(M−H)+.

Example 75

Preparation of N-[(6-fluoro-3'-{[(3S)-3-methyl-1-piperazinyl]methyl}-3-biphenylyl)methyl]-N-(2-N-2-(methyloxy)ethyl]oxy}ethyl)-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl)-4-piperidinyl)methyl]phenyl}carbonyl)amino]methyl}-2'-fluoro-3-biphenylyl)methyl]-2-methyl-1-piperazinecarboxylate (76.1 mg, 0.106 mmol), NaH (8.29 mg, 0.345 mmol) and 1-bromo-2-{[2-(methyloxy)ethyl]oxy}ethane (0.022 mL, 0.160 mmol) in DMF (1.0 mL) were reacted to give the desired product (22.5 mg, 34.2%). EI-MS m/z 617(M−H)+.

Example 76

Preparation of N-[(6-fluoro-3'-{[(3S)-3-methyl-1-piperazinyl]methyl}-3-biphenylyl)methyl]-N-[2-(methyloxy)ethyl]-3-(4-piperidinylmethyl)benzamide Following the general procedure outlined in Example 66, 1,1-dimethylethyl (2S)-4-[(5'-{[({3-[(1-([(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (76.1 mg, 0.106 mmol), NaH (8.29 mg, 0.345 mmol) and 2-bromoethyl methyl ether (0.015 mL, 0.160 mmol) in DMF (1.0 mL) were reacted to give the desired product (16.6 mg, 27.2%). EI-MS m/z 573(M−H)+.

Example 77

Preparation of N-[(6-fluoro-3'-{[(3S)-3-methyl-1-piperazinyl]methyl}-3-biphenylyl)methyl]-N-(3-phenylpropyl)-3-(4-piperidinylmethyl)benzamide Following the general procedure outlined in Example 66, 1,1-dimethylethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (76.1 mg, 0.106 mmol), NaH (8.29 mg, 0.345 mmol) and (3-bromopropyl)benzene (0.024 mL, 0.160 mmol) in DMF (1.0 mL) were reacted to give the desired product (47.2 mg, 70.0%). EI-MS m/z 633(M−H)+.

Preparation 8

The quaternary salts of structures 37 and 38 were prepared as depicted in Scheme 8. The bromo benzaldehyde derivative 33 and (3S)-1-[(3-Bromophenyl)methyl]-3-methylpiperazine 34 were processed to the biphenyl derivative 35 following the chemistry routes outlined in preparation 3. Selective deprotection of the piperazine group of 35 and treatment of the resulting secondary amine gave the quaternary derivative 36. Subsequent removal of the benzyloxy carbonyl protecting group of 36 under acidic conditions afforded compound 37 which in turn can be converted to the tertiary amine 38 by reductive amination with formaldehyde.

Scheme 8
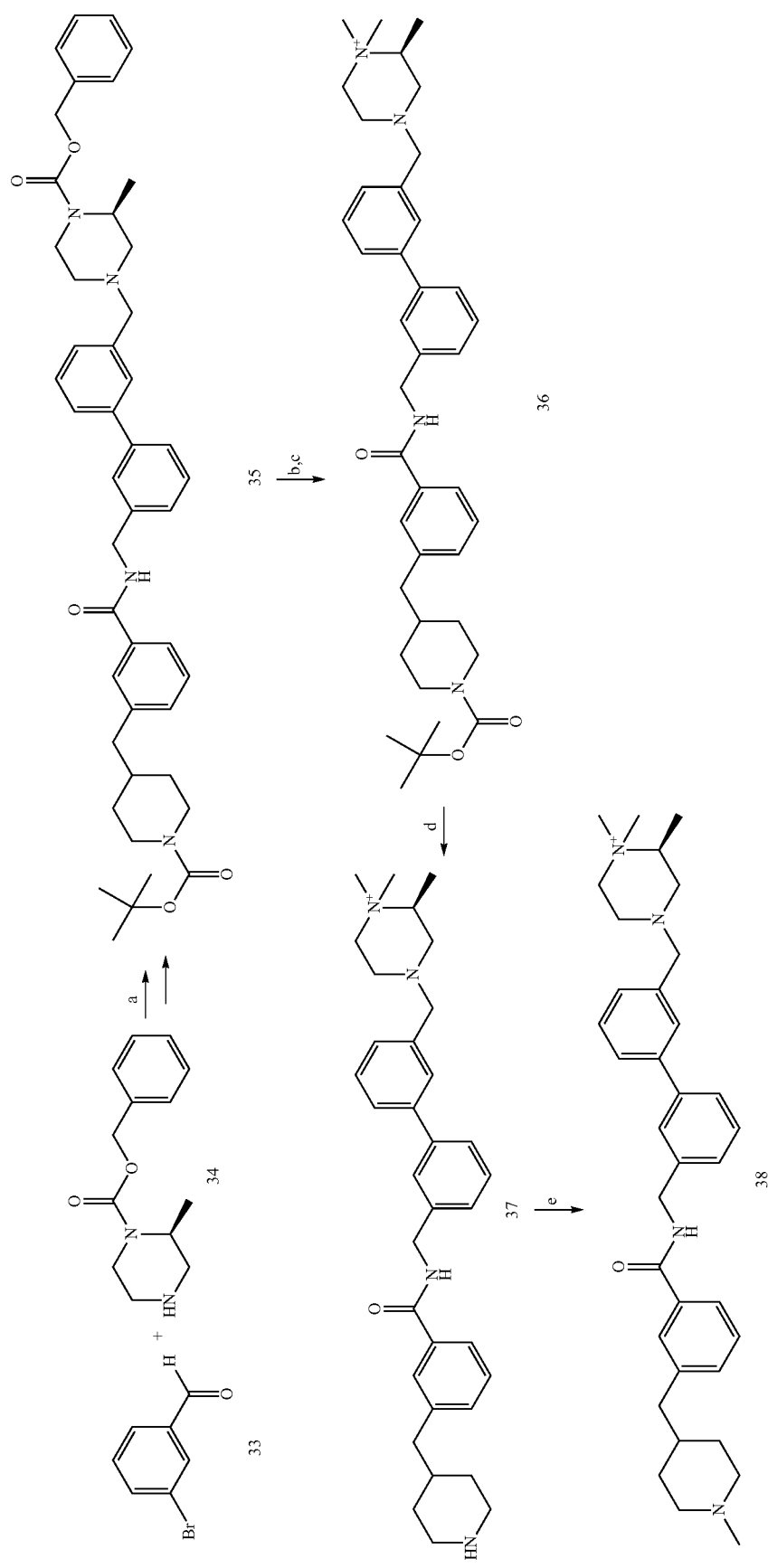
Conditions:
a) see preparation 3;
b) H₂, Pt/C, MeOH;
c) formaldehyde, NaBH₄, MeOH then MeBr in tButyl ether-acetone;
d) MeOH, AcBr;) formaldehyde, NaBH₄, MeOH.

Intermediate 22

1,1-dimethylethyl 4-{[3-({[(6-fluoro-3'-{[(3S)-3-methyl-1-piperazinyl]methyl}-3-biphenylyl)methyl]amino}carbonyl)phenyl]methyl}-1-piperidinecarboxylate

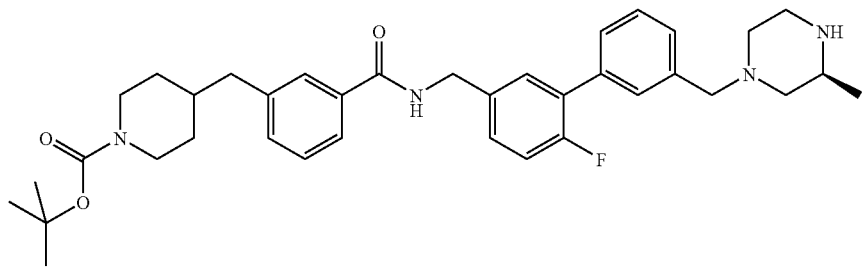

A solution of phenylmethyl (2S)-4-[(5'-{[({3-[(1-{[(1,1-dimethylethyl)oxy]carbonyl}-4-piperidinyl)methyl]phenyl}carbonyl)amino]methyl}-2'-fluoro-3-biphenylyl)methyl]-2-methyl-1-piperazinecarboxylate (1.5 g, 2.0 mmol) and 10% Pd/C (450 mg) in methanol (50 mL) was allowed to react with H₂ at room temperature under atmospheric pressure for 12 hours. The solvent was removed under vacuum. The resulting residue was purified by loading onto 20 g aminopropyl SPE cartridge and eluting sequentially with DCM (3×50 mL), EtOAc (3×50 mL), and MeOH (3×50 mL). The methanol fractions were combined and evaporated to give the title compound as a pale yellow solid (60 mg, 35%). LC/MS: m/z, 615 (M+H), 1.93 min.

Intermediate 23

1,1-dimethylethyl 4-{[3-({[(3'-{[(3S)-3,4-dimethyl-1-piperazinyl]methyl}-6-fluoro-3-biphenylyl)methyl]amino}carbonyl)phenyl]methyl}-1-piperidinecarboxylate

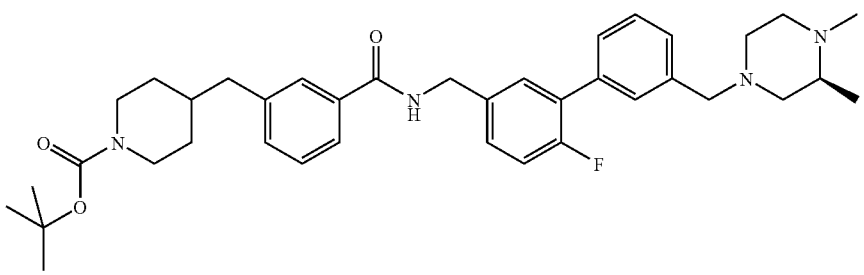

To a solution of 1,1-dimethylethyl 4-{[3-({[(6-fluoro-3'-{[(3S)-3-methyl-1-piperazinyl]methyl}-3-biphenylyl)methyl]amino}carbonyl)phenyl]methyl}-1-piperidinecarboxylate (130 mg, 0.21 mmol) in MeOH (5 mL) was added formaldehyde (37% in water, 69 mg, 0.85 mmol). After 30 minutes stirring at rt, sodium borohydride (16 mg, 0.42 mmol) was added. After stirring at rt for a further 3 hours, the solvent was removed to give a residue which was purified by loading onto a 2 g aminopropyl SPE cartridge and eluting sequentially with DCM (3×5 mL), EtOAc (3×5 mL), and MeOH (3×5 mL). The dichloromethane and ethyl acetate fractions were combined and evaporated to give the title compound (130 mg, 99%). LC/MS: m/z, 629 (M+H), 1.97 min.

Example 78

(2S)-4-({2'-fluoro-5'-[({[3-(4-piperidinylmethyl)phenyl]carbonyl}amino)methyl]-3-biphenylyl}methyl)-1,1,2-trimethylpiperazinyl bromide

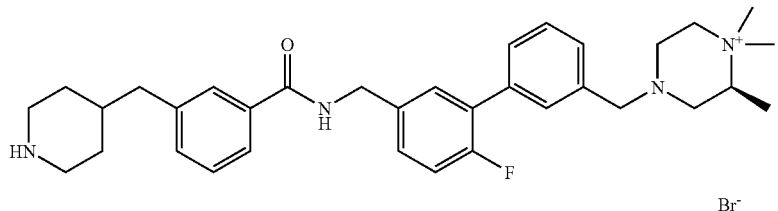

To a solution of 1,1-dimethylethyl 4-{[3-({[(3'-{[(3S)-3,4-dimethyl-1-piperazinyl]methyl}-6-fluoro-3-biphenylyl)methyl]amino}carbonyl)phenyl]methyl}-1-piperidinecarboxylate (130 mg, 0.21 mmol) acetone (2 mL), was added 2M bromomethane in tert-butyl ether (2.1 ml, 4.2 mmol). The mixture was stirred for 16 hours. After removal of the solvent under vacuum, the residue was purified by loading onto a 2 g aminopropyl SPE cartridge and eluting sequentially with DCM (3×5 mL), EtOAc (3×5 mL), and MeOH (3×5 mL). The MeOH fractions were combined, concentrated under vacuum and re-dissolved in DCM (4 mL) and MeOH (1 mL). After cooling to 0° C. with an ice bath, acetyl bromide (4.2 mmol) was added dropwise. After stirring for 1 h, the mixture was evaporated under vacuum to give the title compound (64 mg, 48%). LC/MS: m/z, 543 (M)+, 1.37 min.

Example 79

(2S)-4-F(2'-fluoro-5'-{[({3-[(1-methyl-4-piperidinyl)methyl]phenyl}carbonyl)amino]methyl}-3-biphenylyl)methyl]-1,1,2-trimethylpiperazinyl trifluoroacetate

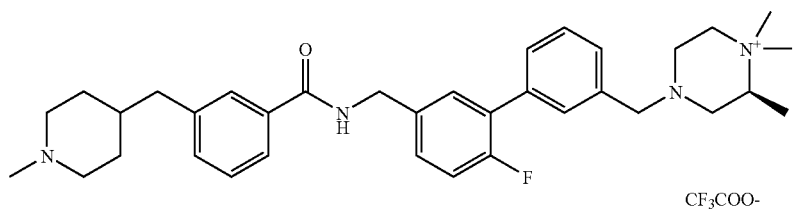

To a solution of (2S)-4-({2'-fluoro-5'-[({[3-(4-piperidinylmethyl)phenyl]carbonyl}amino)methyl]-3-biphenylyl}methyl)-1,1,2-trimethylpiperazinyl bromide (193 mg, 0.31 mmol) in MeOH (5 ml), was added dropwise formaldehyde (37% in water, 100 mg, 1.24 mmol). After stirring at room temperature for 30 min $NaBH_4$ (24 mg, 0.62 mmol) was added. The resulting mixture was stirred at that temperature for 16 hours. After removal of the solvent under vacuum, the residue was purified by Gilson reverse phase HPLC, eluting with acetonitrile/water/0.1% TFA (10/90 to 70/30, v/v, over 12 min), to give the title compound (115 mg, 47%). LC/MS: m/z, 557 (M+H), 1.39 min.

Preparation 9

The compound of structure 42 was prepared as depicted in Scheme 9. The amine derivative 40 and the boronic acid 39 were processed to the biphenyl derivative 41 following the chemistry routes outlined in preparation 4. Reduction of the carbonyl group of 41 with lithium aluminum hydride afforded the secondary amine derivative 42.

Scheme 9

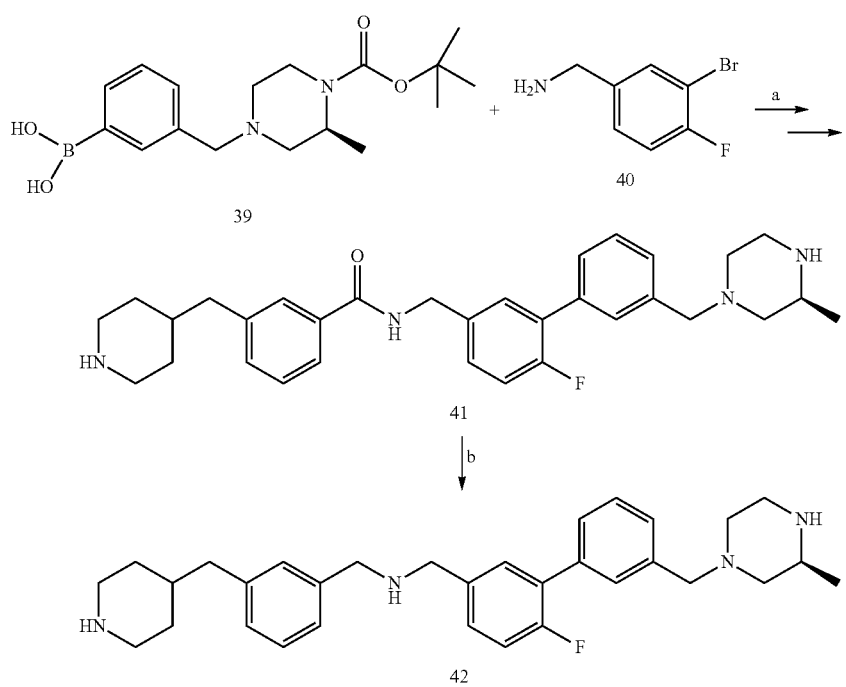

Conditions:
a) see preparation 4,
b) LiAlH₄, THF, mw, 80° C., 1 h.

Example 80

[(6-Fluoro-3'-{[(3S)-3-methyl-1-piperazinyl]methyl}-3-biphenylyl)methyl]{[3(4-piperidinylmethyl)Phenyl]methyl}amine

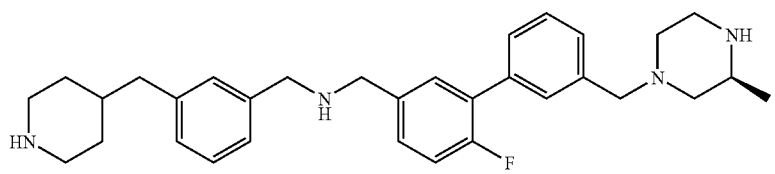

A solution of N-[(6-fluoro-3'-{[(3S)-3-methyl-1-piperazinyl]methyl}-3-biphenylyl)methyl]-3-(4-piperidinylmethyl)benzamide (100 mg, 0.194 mmol) in THF (2.0 mL) was added to lithium aluminum hydride (1.0 N in THF, 2 mL, 2 mmol). The mixture was heated in a microwave reactor at 80° C. for 60 minutes. After cooling to room temperature, the reaction mixture was carefully quenched with saturated Na₂SO₄, filtered through celite, dried over K₂CO₃ and concentrated under vacuum to give a crude oil. Further purification by Gilson reverse phase HPLC, eluting with acetonitrile/water/0.1% TFA (10/90 to 70/30, v/v, over 12 min), gave the title compound (80 mg, 82%) as an oil. LC/MS: m/z, 502 (M+H), 1.29 min.

Preparation 10

The compounds of general structure 17 were prepared in solution phase following the route outlined in Scheme 10.

Firstly, amide coupling of the amine 19 with carboxylic acids gave the corresponding amides 43. Further coupling of 43 with boronic acids 44 using the Suzuki reaction gave biphenyl derivatives 45. Subsequent reduction amination of 45 with protected piperazines 12, followed by removal of the protecting group on the piperazine nitrogen gave the products 17.

Scheme 10

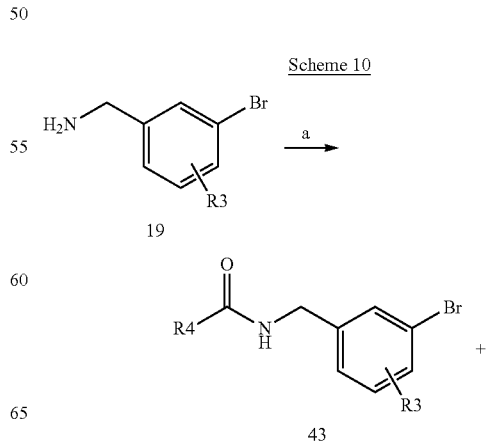

-continued

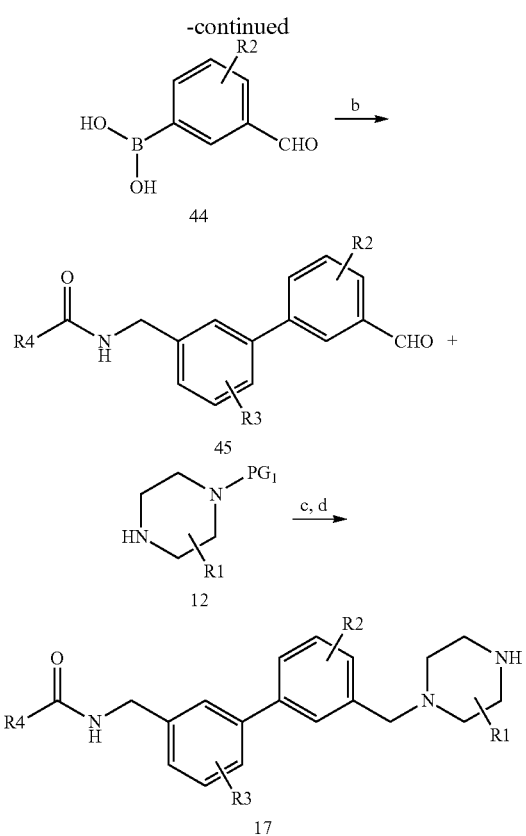

Conditions:
a) HOBt, EDCl, R4CO2H, DMF;
b) Pd(PPh3)4, K2CO3, 1,4-Dioxane, mw, 150° C.;
c) NaB(OAc)3H, DCM, rt;
d) Deprotection of N-piperazine with HCl, TFA or H2/Pd/C.

Intermediate 24

1,1-dimethylethyl 4-{[3-({[(3-bromo-4-fluorophenyl)methyl]amino}carbonyl)phenyl]methyl}-1-piperidinecarboxylate

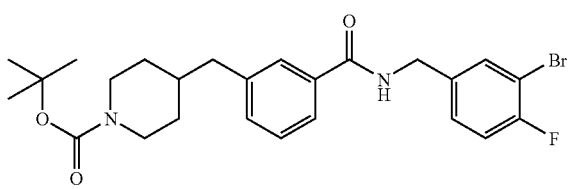

To solution of the commercially available 3-[(1-{[(1,1-dimethylethyl)oxy]carbonyl}-4-piperidinyl)methyl]benzoic acid (200 mg, 0.63 mmol) in CHCl3 (5 mL) was added HOBt (90 mg, 0.67 mmol), EDCI (180 mg, 0.94 mmol), and triethylamine (0.2 ml, 1.4 mmol), followed by [(3-bromo-4-fluorophenyl)methyl]amine hydrochloride (151 mg, 0.62 mmol). The resulting mixture was allowed to stir at room temperature for 2 hours then quenched with saturated aq. NaHCO3 (1 mL) was added. The organic layer was separated, dried over Na2SO4 and evaporated to give a residue which was purified by Combiflash® chromatography eluting with hexane/ethyl acetate (95/5 to 70/30 over 15 min.) to give the title compound as white solid (265 mg, 80%). LC/MS: m/z, 505 (M+H), 2.81 min.

Intermediate 25

1,1-dimethylethyl 4-{[3-({[(6-fluoro-3'-formyl-3-biphenylyl)methyl]amino}carbonyl)phenyl]methyl}-1-piperidinecarboxylate

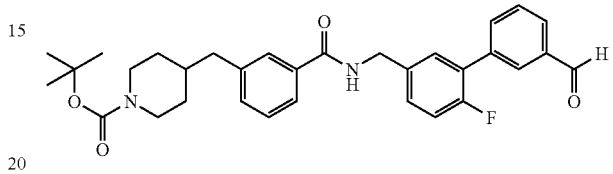

To a solution of 3-formylphenyl)boronic acid (21 mg, 0.14 mmol) in dioxane (3 mL) and water (1 mL) was added 1,1-dimethylethyl 4-{[3-({[(3-bromo-4-fluorophenyl)methyl]amino}carbonyl)phenyl]methyl)-1-piperidinecarboxylate (70 mg, 0.14 mmol), K2CO3 (97 mg, 0.7 mmol) and Pd(PPh3)4 (8 mg, 0.007 mmol). The resulting solution was irradiated in a microwave reactor at 150° C. for 20 minutes then diluted with EtOAc (5 mL). The organic layer was separated and the aqueous layer was further extracted by EtOAc (2×5 mL). The organic layers were combined, dried over Na2SO4, filtered and concentrated under vacuum. The residue was purified by Gilson HPLC, eluting with acetonitrile/water/0.1% TFA (10/90 to 90/10, v/v, over 12 min), to give the title compound (60 mg, 81%). LC/MS: m/z, 531 (M+H), 2.83 min.

Example 81

N-{[6-fluoro-3'-(1-piperazinylmethyl)-3-biphenylyl]methyl}-3-(4-piperidinylmethyl)benzamide

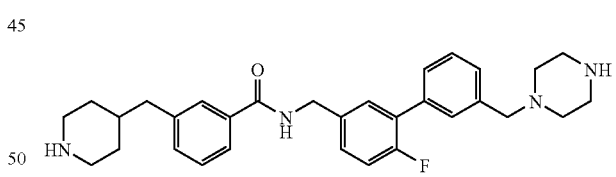

A solution of 1,1-dimethylethyl 4-{[3-({[(6-fluoro-3'-formyl-3-biphenylyl)methyl]amino}carbonyl)phenyl]methyl}-1-piperidinecarboxylate (74 mg, 0.14 mmol) in CH2Cl2 (5 mL) was mixed with 1,1-dimethylethyl (2S)-2-methyl-1-piperazinecarboxylate (26 mg, 0.14 mmol) and NaB(OAc)3H (45 mg, 0.21 mmol). The resulting mixture was stirred for 16 hours, diluted with dichloromethane (30 mL) and washed with brine (10 mL). The organic layer was collected, dried over Na2SO4 and concentrated under vacuum. The residue was purified by loading onto a 2 g amminopropyl SPE cartridge, eluting sequentially with DCM (3×5 mL), EtOAc (3×5 mL), and MeOH (3×5 mL). The DCM fractions were combined, and mixed with 2 mL of TFA. After stirring for 1 h, the mixture was concentrated under vacuum, and the residue thus obtained was purified by Gilson reverse phase HPLC, eluting with acetonitrile/water/0.1% TFA (10/90 to 70/30, v/v, over 12 min), to give the title compound (19 mg, 27%). LC/MS: m/z, 501 (M+H), 1.35 min.

Example 82

N-{[3'-(aminomethyl)-6-fluoro-3-biphenylyl]methyl}-3-(4-piperidinylmethyl)benzamide

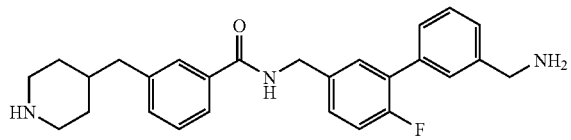

To a solution of {[3-(4,4,5,5-tetramethyl-1,3,2-dioxaborolan-2-yl)phenyl]methyl}amine hydrochloride (54.5 mg, 0.21 mmol) in dioxane (3 mL) and water (1 mL) was added 1,1-dimethylethyl 4-{[3-({[(3-bromo-4-fluorophenyl)methyl]amino}carbonyl)phenyl]methyl}-1-piperidinecarboxylate (100 mg, 0.2 mmol), $K_2CO_3$ (138 mg, 1.0 mmol) and $Pd(PPh_3)_4$ (12 mg, 0.01 mmol). The resulting solution was irradiated in a microwave reactor at 150° C. for 20 minutes then diluted with EtOAc (5 mL). The organic layer was separated and the aqueous layer was further extracted by EtOAc (2×5 mL). The organic layers were combined, dried over $Na_2SO_4$, filtered and concentrated under vacuum. The residue was purified by loading onto a 2 g SCX SPE cartridge and eluting sequentially with DCM (3×5 mL), MeOH (3×5 mL) and MeOH with 2% triethylamine (3×5 mL). The MeOH-triethylamine fractions were combined and evaporated under vacuum. The residue was dissolved in DCM and mixed with TFA (400 μl). After stirring for 2 h at room temperature, the mixture was concentrated under vacuum, and the residue thus obtained was purified by Gilson reverse phase HPLC, eluting with acetonitrile/water/0.1% TFA (5/95 to 85/15, v/v, over 12 min) to give the title compound (30 mg). LC/MS: m/z, 432 (M+H), 1.27 min.

Abbreviations
BOC tert-butyloxycarbonyl
DCM Dichlromethane
DIC 1,3-Dissopropylcarbodiimide
DIPEA Diisopropylethylamine
DMAP Dimethylaminopyridine
DME Dimethoxyethane
DMF Dimethylformamide
DMHB 2,6-dimethoxy-4-polystyrenebenzyloxy-benzaldehyde
DMSO Dimethylsulfoxide
EDCI 1-(3-Dimethylaminopropyl)-3-ethylcarbodiimide hydrochloride
EDC 1-(3-Dimethylaminopropyl)-3-ethylcarbodiimide hydrochloride
ESI Electrospray ionization
EI-MS Electrospray ionization-Mass spectrometry
HATU O-(7-Azabenzotriazol-1-yl)-N,N,N',N'-tetramethyluronium hexafluorophosphate
HOAc Acetic acid
HOBt Hydroxybenzotriazole
HPLC High pressure liquid chromatography
LC/MS Liquid chromatography/Mass spectrometry
MDAP Mass directed automated preparative
mw Microwave
NMP 1-Methyl-2-pyrrolidinone
NMR Nuclear magnetic resonance
rt Room temperature
SPE Solid phase extraction
TEA Triethylamine
TFA Trifluoroacetic acid
THF Tetrahydrofuran

BIOLOGICAL EXAMPLES

The inhibitory effects of compounds at the $M_3$ mAChR of the present invention are determined by the following in vitro and in vivo assays:
Analysis of Inhibition of Receptor Activation by Calcium Mobilization:
1) 384-well FLIPR assay A CHO (chinese hamster ovary) cell line stably expressing the human M3 muscarinic acetylcholine receptor is grown in DMEM plus 10% FBS, 2 mM Glutamine and 200 ug/ml G418. Cells are detached for maintenance and for plating in preparation for assays using either enzymatic or ion chelation methods. The day before the FLIPR (fluorometric imaging plate reader) assay, cells are detached, resuspended, counted, and plated to give 20,000 cells per 384 well in a 50 ul volume. The assay plates are black clear bottom plates, Becton Dickinson catalog number 35 3962. After overnight incubation of plated cells at 37 degrees C. in a tissue culture incubator, the assay is run the next day. To run the assay, media are aspirated, and cells are washed with 1× assay buffer (145 mM NaCl, 2.5 mM KCl, 10 mM glucose, 10 mM HEPES, 1.2 mM $MgCl_2$, 2.5 mM $CaCl_2$, 2.5 mM probenecid (pH 7.4.) Cells are then incubated with 50 ul of Fluo-3 dye (4 uM in assay buffer) for 60-90 minutes at 37 degrees C. The calcium-sensitive dye allows cells to exhibit an increase in fluorescence upon response to ligand via release of calcium from intracellular calcium stores. Cells are washed with assay buffer, and then resuspended in 50 ul assay buffer prior to use for experiments. Test compounds and antagonists are added in 25 ul volume, and plates are incubated at 37 degrees C. for 5-30 minutes. A second addition is then made to each well, this time with the agonist challenge, acetylcholine. It is added in 25 ul volume on the FLIPR instrument. Calcium responses are measured by changes in fluorescent units. To measure the activity of inhibitors/antagonists, acetylcholine ligand is added at an $EC_{80}$ concentration, and the antagonist $IC_{50}$ can then be determined using dose response dilution curves. The control antagonist used with M3 is atropine.
2) 96-well FLIPR assay Stimulation of mAChRs expressed on CHO cells were analyzed by monitoring receptor-activated calcium mobilization as previously described. CHO cells stably expressing $M_3$ mAChRs were plated in 96 well black wall/clear bottom plates. After 18 to 24 hours, media was aspirated and replaced with 100 μl of load media (EMEM with Earl's salts, 0.1% RIA-grade BSA (Sigma, St. Louis Mo.), and 4 μM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 μl of assay buffer (0.1% gelatin (Sigma), 120 mM NaCl, 4.6 mM KCl, 1 mM $KH_2 PO_4$, 25 mM $NaH CO_3$, 1.0 mM $CaCl_2$, 1.1 mM $MgCl_2$, 11 mM glucose, 20 mM HEPES (pH 7.4)). 50 μl of compound ($1×10^{-11}$-$1×10^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 μl of acetylcholine (0.1-10 nM final), prepared in buffer containing 0.1% BSA, at a rate of 50 μl/sec. Calcium mobilization, monitored as change in cytosolic calcium concentration, was measured as change in 566 nm emission intensity. The change in emission intensity is directly related to cytosolic calcium levels. The emitted fluorescence from all 96 wells is measured simultaneously using a cooled CCD camera. Data points are collected every second. This data was then plotting and analyzed using GraphPad PRISM software.

Methacholine-induced Bronchoconstriction

Airway responsiveness to methacholine was determined in awake, unrestrained BalbC mice (n=6 each group). Barometric plethysmography was used to measure enhanced pause (Penh), a unitless measure that has been shown to correlate with the changes in airway resistance that occur during bronchial challenge with methacholine. Mice were pretreated with 50 μl of compound (0.003-10 μg/mouse) in 50 μl of vehicle (10% DMSO) intranasally, and were then placed in the plethysmography chamber. Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software. This experiment allows the determination of duration of activity of the administered compound.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis.

Formulation-Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di- or poly-saccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 μg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurized formulations will generally be retained in a canister (eg an aluminium canister) closed with a valve (eg a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 µm, preferably 2-5 µm. The optimum aerodynamic particle size for inhalation into the alveolar region for achieving systemic delivery to the lung is approximately 0.5-3 µm, preferably 1-3 µm. Particles having an aerodynamic size above 20 µm are generally too large when inhaled to reach the small airways. Average aerodynamic particle size of a formulation may measured by, for example cascade impaction. Average geometric particle size may be measured, for example by laser diffraction, optical means.

To achieve a desired particle size, the particles of the active ingredient as produced may be size reduced by conventional means eg by controlled crystallization, micronisation or nanomilling The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 µm and not less than 15% will have a MMD of less than 15 µm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), anti-static-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, patent Nos. U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound selected from the group consisting of:
N-[(6-fluoro-3'-{[(3S)-3-methyl-1-piperazinyl]methyl }-3-biphenylyl)methyl]-3-[(4-methyl -1-piperazinyl)methyl]benzamide tetra-trifluoroacetate;
3-[(4-methyl-1-piperazinyl)methyl]-N-{[3'-(1-piperazinylmethyl)-3-biphenylyl ]methyl}benzamide tetra-trifluoroacetate;
3-[(4-methyl-1-piperazinyl)methyl]-N-({3'-[(3-methyl-1-piperazinyl)methyl]-3-biphenylyl }methyl)benzamide tetra-trifluoroacetate;
N-[(6-(methyloxy)-3'-{[(3S)-3-methyl-1-piperazinyl]methyl}-3-biphenylyl)methyl]-3-[(4-methyl-1-piperazinyl)methyl]benzamide tetra-trifluoroacetate;

N-[(6-fluoro-3'-{[(3S)-3-methyl-1-piperazinyl]methyl }-3-biphenylyl)methyl]-3-(1-piperazinylmethyl) benzamide tetra-trifluoroacetate;

N-[(6-fluoro-3'-{[(3S)-3-methyl-1-piperazinyl]methyl}-3-biphenylyl)methyl]-3-(hexahydro-1H-1,4-diazepin-1-ylmethyl)benzamide tetra-trifluoroacetate;

3-[(1S,4S)-2,5-diazabicyclo [2.2.1]hept-2-ylmethyl]-N-[(6-fluoro-3'-{[(3S)-3-methyl-1-piperazinyl ]methyl}-3-biphenylyl)methyl]benzamide tetra-trifluoroacetate;

N-[(6-fluoro-3'-{[(3S)-3-methyl-1-piperazinyl]methyl }-3-biphenylyl)methyl]-3-[(3-piperazinyl methyl-1-piperazinyl)methyl]benzamide tetra-trifluoroacetate;

3-{[4-(3-cyanopropyl)-1-piperazinyl]methyl}-N-[(6-fluoro -3'-{[(3S)-3-methyl-1-piperazinyl]methyl}-3-biphenylyl)methyl]benzamide tetra-trifluoroacetate;

4-{[3-({[(6-fluoro-3'-{[(3S)-3-methyl-1-piperazinyl]methyl}-3-biphenylyl) methyl]amino 1carbonyl)phenyl] methyl}-2-piperazine carboxamide tetra-trifluoro acetate;

N-[(6-fluoro-3'-{[(3S)-3-methyl-1-piperazinyl]methyl}-3-biphenylyl)methyl]-3-({4-[3-(methyloxy) propyl]-1-piperazinyl}methyl)benzamide tetra trifluoroacetate;

N-[(6-fluoro -3'-{[(3S)-3-methyl-1-piperazinyl]methyl }-3-biphenylyl)methyl]-3-[(4-methyl -1-piperidinyl)methyl]benzamide tri-trifluoroacetate;

N-[(6-fluoro-3'-{[(3S)-3-methyl-1-piperazinyl]methyl}-3-biphenylyl)methyl]-3-({4-[2-(phenyloxy) ethyl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-{[4-(3-hydroxypropyl) -1-piperazinyl]methyl}benzamide tetra-trifluoroacetate;

3-({2-[(dimethylamino)methyl]-1-piperidinyl}methyl)-N-[(6-fluoro-3'-{[(3S)-3-methyl-1-piperazinyl ]methyl}-3-biphenylyl)methyl]benzamide tetra-trifluoroacetate;

N-[(6-fluoro-3'-{[(3S)-3-methyl-1-piperazinyl]methyl }-3-biphenylyl)methyl]-3-(4-morpholinylmethyl) benzamide tri-trifluoroacetate;

3-[(2,5-dimethyl-1-piperazinyl)methyl]-N-[(6-fluoro-3'-{[(3S)-3-methyl-1-piperazinyl ]methyl}-3-biphenylyl) methyl]benzamide tetra-trifluoroacetate;

N-[(6-fluoro -3'-{[(3S)-3-methyl-1-piperazinyl]methyl}-3-biphenylyl)methyl]-3-{[(1S,4 5)-5-methyl-2,5-diazabicyclo [2.2.1]hept-2-yl]methyl}benzamide tetra-trifluoroacetate;

N-[(6-fluoro-3'-{[(3S)-3-methyl-1-piperazinyl]methyl }-3-biphenylyl)methyl]-3-[(4-formyl -1-piperazinyl)methyl]benzamide tri-trifluoroacetate;

3-{[[3-(dimethylamino)propyl](methyl)amino]methyl}-N-[(6-fluoro -3'-{[(35)-3-methyl -1-piperazinyl]methyl}-3-biphenylyl)methylTh enz amide tetra-trifluoroacetate;

N-[(6-fluoro-3'-{[(3S)-3-methyl-1-piperazinyl]methyl}-3-biphenylyl)methyl]-3-{[4-(1-methyl -4-piperidinyl)-1-piperazinyl]methyl}benzamide penta-trifluoroacetate;

3-{[[2-(dimethylamino)ethyl](methyl)amino]methyl}-N-[(6-fluoro-3'-{[(3S)-3-methyl-1-piperazinyl ]methyl}-3-biphenylyl)methyl]benzamide tetra-trifluoroacetate;

N-[(6-fluoro -3'-{[(3S)-3-methyl-1-piperazinyl]methyl }-3-biphenylyl)methyl]-3-({4-[(2E)-3-phenyl-2-propen-1-yl]-1-piperazinyl}methyl)benzamide tetra-trifluoroacetate;

N-[(6-fluoro-3'-{[(3S)-3-methyl-1-piperazinyl]methyl }-3-biphenylyl)methyl]-3-[(4-methylhexahydro -1H-1,4-diazepin-1-yl)methyl]benzamide tetra-trifluoroacetate;

3-[(dimethylamino)methyl]-N-[(6-fluoro-3'-{[(3S)-3-methyl-1-piperazinyl]methyl}-3-biphenylyl) methyl]benzamide tri-trifluoroacetate;

N-[(6-fluoro-3'-{[(3S)-3-methyl-1-piperazinyl]methyl}-3-biphenylyl)methyl]-3-({4-[2-(4-morpholinyl) ethyl]-1-piperazinyl}methyl)benzamide penta-trifluoroacetate;

3-[(diethylamino)methyl]-N-[(6-fluoro-3'-{[(3S)-3-methyl-1-piperazinyl]methyl}-3-biphenylyl) methyl]benzamide tri-trifluoroacetate;

3-({4-[2-(dimethylamino)ethyl]-1-piperidinyl}methyl)-N-[(6-fluoro-3'-{[(3S)-3-methyl -1-piperazinyl]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[2-(1-pyrrolidinyl) ethyl]-1-piperazinyl}methyl)benzamide p enta-trifluoro acetate;

N-[(6-fluoro-3'-{[(3S)-3-methyl-1-piperazinyl]methyl }-3-biphenylyl)methyl]-3-(1-piperidinylmethyl) benzamide tri-trifluoroacetate;

N-[(6-fluoro-3'-{[(3S)-3-methyl-1-piperazinyl]methyl }-3-biphenylyl)methyl]-3-[(1-methyl -1,7-diazaspiro [4.4]non-7-yl)methyl]benzamide tetra-trifluoroacetate;

3-{[bis(phenylmethyl)amino]methyl}-N-[(6-fluoro-3'-{[(3S)-3-methyl-1-piperazinyl ]methyl}-3-biphenylyl) methyl]benzamide tri-trifluoroacetate;

3-(dimethylamino)-N-({3'-[(3-methyl-1-piperazinyl)methyl]-3-biphenylyl }methyl)benzamide tri-trifluoroacetate;

3-(dimethylamino)-N-{[3'-(1-piperazinylmethyl)-3-biphenylyl]methyl}benzamide tri-trifluoroacetate; and 3-amino-N-{[3'-(1-piperazinylmethyl)-3-biphenylyl] methyl}benzamide tri-trifluoroacetate;

or any other pharmaceutically acceptable salt, or free base thereof.

2. A compound selected from the group consisting of:

N-[(6-fluoro-3'-{[(3S)-3-methyl-1-piperazinyl]methyl }-3-biphenylyl)methyl]-3-[(4-methyl -1-piperazinyl)methyl]benzamide tetra-trifluoroacetate;

3-[(4-methyl-1-piperazinyl)methyl]-N-{[3'-(1-piperazinylmethyl)-3-biphenylyl ]methyl}benzamide tetra-trifluoroacetate;

3-[(4-methyl-1-piperazinyl)methyl]-N-({3'-[(3-methyl-1-piperazinyl)methyl]-3-biphenylyl }methyl)benzamide tetra-trifluoroacetate;

N-[(6-(methyloxy)-3'-{[(3S)-3-methyl-1-piperazinyl]methyl}-3-biphenylyl)methyl]-3-[(4-methyl-1-piperazinyl)methyl]benzamide tetra-trifluoroacetate;

N-[(6-fluoro -3'-{[(3S)-3-methyl-1-piperazinyl]methyl }-3-biphenylyl)methyl]-3-(1-piperazinylmethyl) benzamide tetra-trifluoroacetate;

N-[(6-fluoro -3'-{[(3S)-3-methyl-1-piperazinyl]methyl}-3-biphenylyl)methyl]-3-(hexahydro -1H-1,4-diazepin-1-ylmethyl)benzamide tetra-trifluoroacetate;

3-[(1S,4S)-2,5-diazabicyclo [2.2.1]hept-2-ylmethyl]-N-[(6-fluoro -3'-{[(3S)-3-methyl-1-piperazinyl ]methyl}-3-biphenylyl)methyl]benzamide tetra-trifluoroacetate;

N-[(6-fluoro-3'-{[(3S)-3-methyl-1-piperazinyl]methyl }-3-biphenylyl)methyl]-3-[(3-methyl -1-piperazinyl)methyl T h enzamide tetra tri-fluoroacetate;

3-{[4-(3-cyanopropyl)-1-piperazinyl]methyl}-N-[(6-fluoro -3'-{[(3S)-3-methyl-1-piperazinyl ]methyl}-3-biphenylyl)methyl]benzamide tetra-trifluoroacetate;

4-{[3-({[(6-fluoro-3'-{[(3S)-3-methyl-1-piperazinyl]methyl}-3-biphenylyl) methyl]amino 1carbonyl)phenyl]methyl}-2-piperazinecarboxamide tetra-trifluoroacetate;

N-[(6-fluoro -3'-{[(3S)-3-methyl-1-piperazinyl]methyl}-3-biphenylyl)methyl]-3-({4-[3-(methyloxy) propyl]-1-piperazinyl}methyl)benzamide tetra trifluoroacetate;

N-[(6-fluoro-3'-{[(3S)-3-methyl-1-piperazinyl]methyl}-3-biphenylyl)methyl]-3-[(4-methyl -1-piperidinyl)methyl]benzamide tri-trifluoroacetate;

N-[(6-fluoro-3'-{[(3S)-3-methyl-1-piperazinyl]methyl}-3-biphenylyl)methyl]-3-({4-[2-(phenyloxy) ethyl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-{[4-(3-hydroxypropyl) -1-piperazinyl]methyl}benzamide tetra-trifluoroacetate;

3-({2-[(dimethylamino)methyl]-1-piperidinyl}methyl)-N-[(6-fluoro-3'-{[(3S)-3-methyl-1-piperazinyl ]methyl}-3-biphenylyl)methyl]benzamide tetra-trifluoroacetate;

N-[(6-fluoro -3'-{[(3S)-3-methyl-1-piperazinyl]methyl}-3-biphenylyl)methyl]-3-(4-morpholinylmethyl) benzamide tri-trifluoroacetate;

3-[(2,5-dimethyl-1-piperazinyl)methyl]-N-[(6-fluoro-3'-{[(3S)-3-methyl-1-piperazinyl ]methyl}-3-biphenylyl) methyl]benzamide tetra-trifluoroacetate;

N-[(6-fluoro-3'-{[(3S)-3-methyl-1-piperazinyl]methyl}-3-biphenylyl)methyl]-3-{[(1S,4 5)-5-methyl-2,5-diazabicyclo [2.2.1]hept-2-yl]methyl}benzamide tetra-trifluoroacetate;

N-[(6-fluoro-3'-{[(3S)-3-methyl-1-piperazinyl]methyl}-3-biphenylyl)methyl]-3-[(4-formyl -1-piperazinyl)methyl]benzamide tri-trifluoroacetate;

3-{[[3-(dimethylamino)propyl](methyl)amino]methyl}-N-[(6-fluoro-3'-{[(3S)-3-methyl -1-piperazinyl]methyl}-3-biphenylyl)methylTh enz amide tetra-trifluoroacetate;

N-[(6-fluoro-3'-{[(3S)-3-methyl-1-piperazinyl]methyl}-3-biphenylyl)methyl]-3-{[4-(1-methyl -4-piperidinyl)-1-piperazinyl]methyl}benzamide penta-trifluoroacetate;

3-{[[2-(dimethylamino)ethyl](methyl)amino]methyl}-N-[(6-fluoro-3'-{[(3 5)-3-methyl-1-piperazinyl ]methyl}-3-biphenylyl)methyl]benzamide tetra-trifluoroacetate;

N-[(6-fluoro-3'-{[(3S)-3-methyl-1-piperazinyl]methyl}-3-biphenylyl)methyl]-3-({4-[(2E)-3-phenyl-2-prop en-1-yl]-1-piperazinyl}methyl)benzamide tetra-trifluoroacetate;

N-[(6-fluoro-3'-{[(3S)-3-methyl-1-piperazinyl]methyl}-3-biphenylyl)methyl]-3-[(4-methylhexahydro -1H-1,4-diazepin-1-yl)methyl]benzamide tetra-trifluoroacetate;

3-[(dimethylamino)methyl]-N-[(6-fluoro-3'-{[(3S)-3-methyl-1-piperazinyl]methyl}-3-biphenylyl) methyl]benzamide tri-trifluoroacetate;

N-[(6-fluoro-3'-{[(3S)-3-methyl-1-piperazinyl]methyl}-3-biphenylyl)methyl]-3-({4-[2-(4-morpholinyl) ethyl]-1-piperazinyl}methyl)benzamide penta-trifluoroacetate;

3-[(diethylamino)methyl]-N-[(6-fluoro-3'-{[(3S)-3-methyl-1-piperazinyl]methyl}-3-biphenylyl)methyl]benzamide tri-trifluoroacetate;

3-({4-[2-(dimethylamino)ethyl]-1-piperidinyl}methyl)-N-[(6-fluoro-3'-{[(3S)-3-methyl -1-piperazinyl]methyl}-3-biphenylyl)methylTh enz amide tetra-trifluoroacetate;

N-[(6-fluoro-3'-{[(3S)-3-methyl-1-piperazinyl]methyl}-3-biphenylyl)methyl]-3-({4-[2-(1-pyrrolidinyl)ethyl]-1-piperazinyl}methyl)benzamide penta-trifluoroacetate;

N-[(6-fluoro-3'-{[(3S)-3-methyl-1-piperazinyl]methyl }-3-biphenylyl)methyl]-3-(1-piperidinylmethyl)benzamide tri-trifluoroacetate;

N-[(6-fluoro-3'-{[(3S)-3-methyl-1-piperazinyl]methyl }-3-biphenylyl)methyl]-3-[(1-methyl-1 ,7-diazaspiro [4.4]non-7-yl)methylTh enz amide tetra-trifluoroacetate;

N-[(6-fluoro-3'-{[(3S)-3-methyl-1-piperazinyl]methyl 1-3-biphenylyl)methyl]-3-(4-piperidinylmethyl)benzamide; and N-[(3'-{[(3S)-3-methyl-1-piperazinyl]methyl 1-3-biphenylyl)methyl]-3-(4-piperidinylmethyl)benzamide;

or a pharmaceutically acceptable salt, or free base thereof.

3. A pharmaceutical composition comprising a compound according to claim 1, or any other pharmaceutically acceptable salt, or free base thereof, and a pharmaceutically acceptable carrier or excipient.

4. A pharmaceutical composition comprising a compound according to claim 2, or a pharmaceutically acceptable salt, or free base thereof, and a pharmaceutically acceptable carrier or excipient.

* * * * *